US006383764B1

(12) United States Patent
Civelli et al.

(10) Patent No.: US 6,383,764 B1
(45) Date of Patent: May 7, 2002

(54) METHODS OF IDENTIFYING COMPOUNDS FOR CONTROLLING ABSENCE SEIZURES IN A MAMMAL RELATING TO PROLACTIN-RELEASING PEPTIDE(PRRP)

(75) Inventors: Olivier Civelli, Irvine; Steven Lin, Upland, both of CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/560,915

(22) Filed: Apr. 28, 2000

(51) Int. Cl.$^7$ .................. G01N 33/53; G01N 33/566; A61K 38/00

(52) U.S. Cl. .................. 435/7.8; 435/7.2; 514/2; 436/501

(58) Field of Search .................. 436/503, 517, 436/501; 514/2; 435/7.2, 7.21, 7.8

(56) References Cited

FOREIGN PATENT DOCUMENTS

| WO | WO97/24436 | 2/1997 | ............ C12N/15/12 |
| WO | WO98/58962 | 12/1998 | ......... C07K/14/575 |

OTHER PUBLICATIONS

Freshney, RI Culture of Animal Cells: A Manual of Basic Technique. Alan R. Liss, Inc. (1983) New York.*
Chen et al., "Prolactin–releasing peptide–immunoreactivity in A1 and A2 noradrenergic neurons of the rat medulla" *Brain Research*, 822:276–279.
Civelli et al., "Orphan receptors, novel neuropeptides and reverse pharmaceutical research" *Brain Research*, 848:63–65 (1999).
Danober et al., "Pathophysiological mechanisms of genetic absence epilepsy in the rat" *Progress in Neurobiol.*, 55:27–57 (1998).
Dong et al., "GRIP: a synaptic PDZ domain–containing protein that interacts with AMPA receptors" *Nature.*, 386:279–284 (1997).
Dong et al., "Characterizaton of the glutamate receptor–interacting proteins GRIP1 and GRIP2" *J. of Neurosci.*, 19(16) :6930–6941 (1999).
Egleton and Davis, "Bioavailability and transport of peptides and peptide drugs into the brain" *Peptides*, 18:1431–1439 (1997).
Fujii et al., "Tissue distribution of prolactin–releasing peptide (PrRP) and its receptor" *Regulatory Peptides*, 83:1–10 (1999).
Fujimoto et al., "Isolation and characterization of a novel bioactive peptide, carassius RFamide (C–RFa), from the brain of the Japanese crucian carp" *Biochem. & Biophysic. Research Comm.*, 242:436–440 (1998).
Hinuma et al., "A prolactin–releasing peptide in the brain" *Nature*, 393:272–276 (1998).

Horwell, "The 'peptoid'approach to the design of the non–peptide, small molecule agonists and antagonists of neuropeptides" *Trends Biotechnol.*, 13:132–134 (1995).
Iwasa et al., "Altered expression levels of G protein subclass mRNAs in various seizures stages of the kindling model" *Brain Research*, 818: 570–574 (1999).
Kieber–Emmons et al., "Therapeutic peptides and peptidomimetrics" *Current Opinion in Biotechnology*, 8:435–441 (1997).
Lin et al., "Prolactin releasing peptide (PRRP) suppresses absence seizures by modulating neurotransmission through AMPA receptors" Society for Neuroscience, 29$^{th}$ Annual Meeting, Oct. 23–28, 1999, Abstract 387.6 (1999).
Liu et al., "Evidence for a critical role of GABAergic transmission within the thalamus in the genesis and control of absence seizures in the rat" *Brain Research*, 545:1–7 (1991).
Marchese et al., "Cloning and chromosomal mapping of three novel genes, GPR9, GPR10, and GPR14, encoding receptors related to interleukin 8, neuropeptide Y and somatostatin receptors" *Genomics*, 29:335–344 (1995).
Maruyama et al., "Immunocytochemical localization of prolactin–releasing peptide in the rat brain" *Endocrinology*, 140(5) :2326–2333 (1999).
Matsumoto et al., "Stimulation of prolactin release by prolactin–releasing peptide in rats" *Biochem. & Biophysic. Research Comm.*, 259:321–324 (1999).
Matsumoto et al., "Distribution and characterization of immunoreactive prolactin–releasing peptide (PrRP) in rat tissue and plasma" *Biochem. & Biophysic. Research Comm.*, 257:264–268 (1999).

(List continued on next page.)

* cited by examiner

*Primary Examiner*—Elizabeth Kemmerer
*Assistant Examiner*—Regina M. DeBerry
(74) *Attorney, Agent, or Firm*—Campbell & Flores LLP

(57) ABSTRACT

The invention provides a substantially pure Prolactin Releasing Peptide (PrRP) functional analog which suppresses absence seizures in a mammal, and related pharmaceutical compositions. The invention also provides a method of controlling absence seizures in a mammal, by administering to a mammal susceptible to absence seizures an effective amount of PrRP or a PrRP functional analog. Also provided are methods of identifying a compound that modulates AMPA receptor signaling in a mammal, by providing a compound that is a PrRP or PrRP functional analog, and determining the ability of the compound to modulate AMPA receptor signaling. The invention also provides methods of identifying a compound for controlling absence seizures in a mammal, by providing a compound that is a PrRP or PrRP functional analog, and determining the ability of the compound to control absence seizures in a mammal. Also provided are pharmaceutical compositions for controlling absence seizures in a mammal. The compositions and related methods contain a compound identified by the methods of the invention as a compound that modulates AMPA receptor signaling or as a compound that controls absence seizures.

13 Claims, 8 Drawing Sheets

OTHER PUBLICATIONS

McCormick and Bal, "Sleep and Arousal : Thalamorcortical Mechanisms" *Annual Review of Neuroscience,* 20:185–215 (1997).

Minami et al., "Cellular localization of prolactin–releasing peptide messenger RNA in the rat brain" *Neuroscience Letters,* 266:73–75 (1999).

Roland et al., "Anatomical distribution of prolactin–releasing peptide and its receptor suggests additional functions in the central nervous system and periphery" *Endocrinology,* 140:5736–5745 (199).

Snead, O. Carter, "Evidence for G protein modulation of experimental–generalized absence seizures in rat" *Neuroscience Letters,* 148:15–18 (1992).

Srivastava et al., "Novel anchorage of GluR2/3 to the Postsynaptic density by the AMPA receptor–binding protein ABP" *Neuron,* 21:581–591 (1998).

Tsunoda et al., "A multivalent PDZ–domain protein assembles signalling complexes in a G–protein–coupled cascade" *Nature,* 338:243–249 (1997).

Welch et al., "Sequence and tissue distribution of a candidate G–Coupled receptor cloned from rat hypothalamus" *Biochem. & Biophysic. Research Comm.,* 209(2) :606–613 (1995).

Wilson et al., "Orphan G–protein coupled receptors: the next generation of drug targets?" *Brit. J. of Pharmacol.,* 125:1387–1392 (1998).

Xia et al., "Clustering of AMPA receptors by the synaptic PDZ domain–containing protein PICK1 "*Neuron,* 22:179–187 (1999).

GPR10 tail    -  FREELRKLLVAWPRKIAPHGQNMTVSVVI.
GLuR2 tail    -  NPSSSQNSQNFAATYKEGYNYYGIESVKI.
GLuR3 tail    -  FKPAPATNTQNYATYREGYNVYGTESVKI.

1) Flag GPR10 WT------------PHGQNMTVSVVI.
2) Flag GPR10 de16----------PHGQNM.
3) Flag GPR10 ΔLC-----------PHGQNMTVPRPA.
4) Flag GPR10 T365A---------PHGQNMAVSVVI.
5) Flag GPR10 V366A---------PHGQNMTASVVI.
6) Flag GPR10 S367A---------PHGQNMTVAVVI.
7) Flag GPR10 V368A---------PHGQNMTVSAVI.
8) Flag GPR10 V369A---------PHGQNMTVSVAI.
9) Flag GPR10 I370A---------PHGQNMTVSVVA.

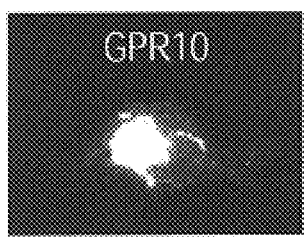 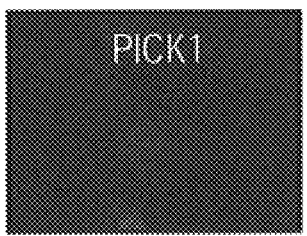 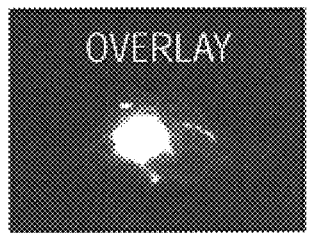
FIG. 3B-1  FIG. 3B-2  FIG. 3B-3
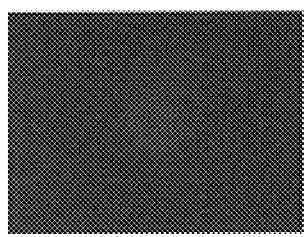 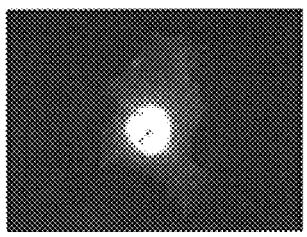 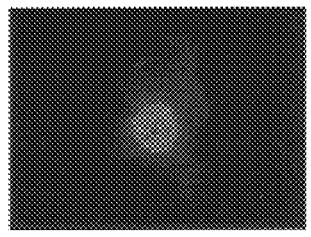
FIG. 3C-1  FIG. 3C-2  FIG. 3C-3
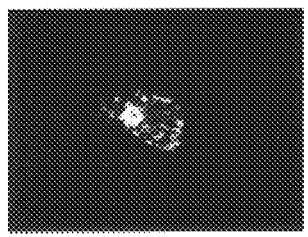 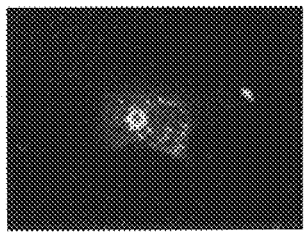 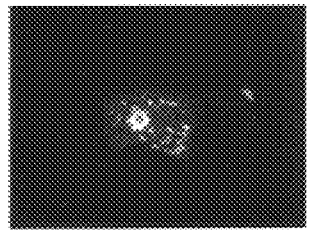
FIG. 3D-1  FIG. 3D-2  FIG. 3D-3
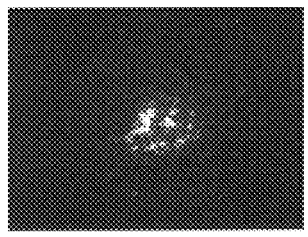 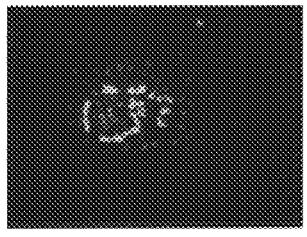 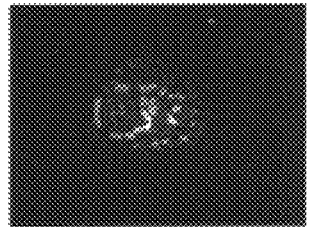
FIG. 3E-1  FIG. 3E-2  FIG. 3E-3
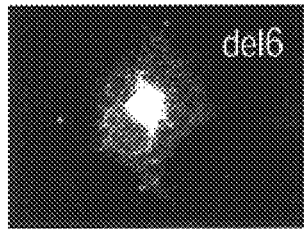 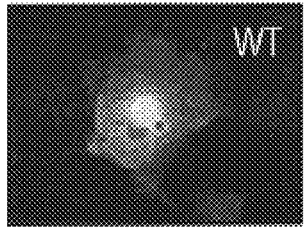 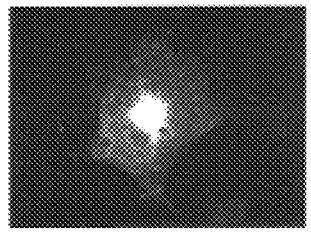
FIG. 3F-1  FIG. 3F-2  FIG. 3F-3
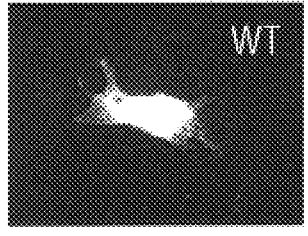 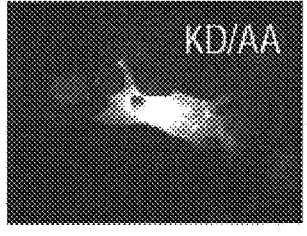 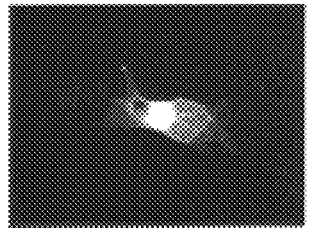
FIG. 3G-1  FIG. 3G-2  FIG. 3G-3

METHODS OF IDENTIFYING COMPOUNDS FOR CONTROLLING ABSENCE SEIZURES IN A MAMMAL RELATING TO PROLACTIN-RELEASING PEPTIDE (PRRP)

This invention was made in part with U.S. Government support under Grant No. NIH MH60231. The U.S. Government may have certain rights in this invention.

BACKGROUND OF THE INVENTION

1. Field of the Invention

The present invention relates generally to the field of medicine and, more specifically, to therapeutic compositions and methods relating to Prolactin Releasing Peptide (PrRP).

2. Background Information

Epilepsy is a common condition, estimated to affect from 40 to 100 million people worldwide, and from 2 to 2.5 million Americans. Of the several clinically recognized forms of epilepsy., juvenile myoclonus epilepsy (JME) accounts for about 10% to 30% of the-cases, and childhood absence epilepsy (CAE) accounts for a further 5% to 15%. Both JME and CAE are associated with a form of seizures called "generalized absence seizures" or "petit mal seizures."

Absence seizures are generalized non-convulsive seizures characterized by a brief period of unresponsiveness to environmental stimuli and cessation of activity, that can occur as frequently as several hundred times a day, primarily during quiet wakefulness, inattention and the transition between sleep and waking. In patients with absence seizures, generalized tonic-clonic seizures (GTCS) or "grand mal seizures" occasionally develop.

Currently available drugs to control absence seizures are often associated with adverse side effects, including gastrointestinal symptoms, tremors, sedation, temporary hair loss, dizziness, incoordination, rashes, and drug interaction complications. More seriously, potentially fatal hepatic and hematopoietic complications, as well as teratogenicity (e.g. neural tube birth defects), have been associated with absence seizure medications. Additionally, while currently available drugs are effective in many individuals, certain individuals are resistant to all known treatments.

Thus, there exists a need to identify new therapeutic agents that can be used to control absence seizures, which will significantly improve the quality of life of patients suffering from this disorder. Such drugs will likely also be effective in ameliorating conditions associated with parts of the brain responsible for absence seizures, or in diseases that share the underlying biochemical pathway of absence seizures. However, in order to rapidly screen for new drugs for controlling absence seizures, or to rationally design such drugs, it is necessary to first understand the biochemical mechanism that underlies absence seizures, and to provide appropriate assay systems for testing for new drugs. The present invention satisfies these needs and provides related advantages as well.

SUMMARY OF THE INVENTION

The invention provides a substantially pure Prolactin Releasing Peptide (PrRP) functional analog which suppresses absence seizures in a mammal, and pharmaceutical compositions containing the PrRP functional analog.

The invention also provides a method of controlling absence seizures in a mammal, by administering to a mammal susceptible to absence seizures an effective amount of PrRP or a PrRP functional analog.

Also provided are methods of identifying a compound that modulates AMPA receptor signaling in a mammal. The methods are practiced by providing a compound that is a PrRP or PrRP functional analog, and determining the ability of the compound to modulate AMPA receptor signaling.

In one method of identifying a compound that modulates AMPA receptor signaling in a mammal, a compound that is a PrRP or PrRP functional analog is provided by contacting a PrRP receptor with one or more candidate compounds under conditions wherein PrRP promotes a predetermined signal, identifying a compound that promotes production of the predetermined signal, and providing the compound. In an alternative method, a compound that is a PrRP or PrRP functional analog is provided by contacting a PrRP receptor with one or more candidate compounds under conditions wherein PrRP binds the PrRP receptor, identifying a compound that binds the PrRP receptor, and providing the compound.

In one method of identifying a compound that modulates AMPA receptor signaling in a mammal, the ability of the PrRP or PrRP functional analog to modulate AMPA receptor signaling is determined by contacting a thalamic preparation with the compound, and determining AMPA receptor mediated oscillatory activity in the preparation. In an alternative method, the ability of the PrRP or PrRP functional analog to modulate AMPA receptor signaling is determined by contacting a cell with the compound, and determining AMPA receptor mediated currents in the cell. In a further alternative method, the ability of the PrRP or PrRP functional analog to modulate AMPA receptor signaling is determined by contacting a cell with the compound, and determining AMPA receptor mediated ion influx into the cell.

Also provided are pharmaceutical compositions for controlling absence seizures in a mammal, containing a compound identified by the methods of the invention as a compound that suppresses AMPA receptor signaling. Further provided are methods of controlling absence seizures in a mammal by administering to a mammal susceptible to absence seizures an effective amount of such pharmaceutical compositions.

The invention also provides methods of identifying a compound for controlling absence seizures in a mammal. The methods are practiced by providing a compound that is a PrRP or PrRP functional analog, and determining the ability of the compound to control absence seizures in a mammal.

In one method of identifying a compound for controlling absence seizures in a mammal, a compound that is a PrRP or PrRP functional analog is provided by contacting a PrRP receptor with one or more candidate compounds under conditions wherein PrRP promotes a predetermined signal, identifying a compound that promotes production of the predetermined signal, and providing the compound. In an alternative method, a compound that is a PrRP or PrRP functional analog is provided by contacting a PrRP receptor with one or more candidate compounds under conditions wherein PrRP binds the PrRP receptor, identifying a compound that binds the PrRP receptor, and providing the compound.

In one method of identifying a compound for controlling absence seizures in a mammal, the ability of the PrRP or PrRP functional analog to control absence seizures is practiced by administering the compound to a mammal susceptible to absence seizures, and determining seizure activity in the mammal.

Also provided are pharmaceutical compositions for controlling absence seizures in a mammal, containing a compound identified by the methods of the invention as a compound for controlling absence seizures. Further provided are methods of controlling absence seizures in a mammal by administering to a mammal susceptible to absence seizures an effective amount of such pharmaceutical compositions.

BRIEF DESCRIPTION OF THE DRAWINGS

FIG. 2B, bottom, shows GRIP expression in the crude lysate.

FIG. 2D, middle, shows GRIP expression in the crude lysate. FIG. 2D, shows GPR10 expression in the co-immunoprecipitated samples.

FIG. 2F, bottom, shows expression of the indicated proteins in crude lysates.

FIG. 3B shows the expression pattern of GPR10 in COS7 cells transfected with GPR10 alone.

FIG. 3C shows the expression pattern of PICK1 in COS7 cells transfected with PICK1 alone.

FIG. 3D shows cytoplasmic clusters of GPR10 and PICK1 in COS7 cells co-transfected with GPR10 and PICK1.

FIG. 3E shows cell surface clusters of GPR10 and PICK1 in COS7 cells co-transfected with GPR10 and PICK1.

FIG. 3F shows the expression pattern of a GPR10 mutant (del6) and PICK1 in COS7 cells co-transfected with GPR10 (del6) and PICK1.

FIG. 3G shows the expression pattern of GPR10 and a PICK1 mutant (KD/AA) in COS7 cells co-transfected with GPR10 and PICK1 (KD/AA).

DETAILED DESCRIPTION OF THE INVENTION

Figure 1A:
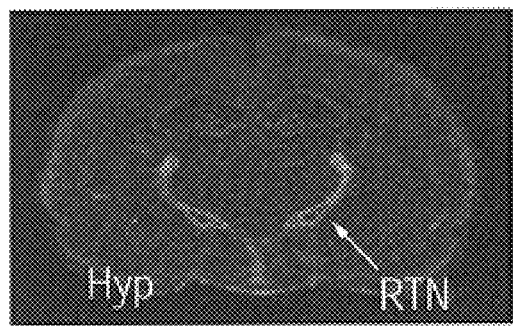
FIGS. 1A and 1B show expression of GPR10 RNA on coronal and horizontal sections, respectively, of adult rat brains. Abbreviations are RTN: reticular thalamic nucleus; Hyp: Hypothalamic nuclei; SA: Shell, nucleus accumbens.

The present invention relates to the determination that PrRP modulates the activity of the reticular thalamic nucleus (RTN), a region of the brain implicated in sleep rhythms, attention processing and absence seizures, through a functional interaction between the PrRP receptor (GPR10), and Alpha-amino-3-hydroxy-5-methyl-4-isoxazolepropionic acid (AMPA) receptors. The inventors have determined that PrRP specifically reduces AMPA receptor mediated oscillatory activity in the RTN, and effectively suppresses absence seizures in mammals.

Thus, based on the determination of an important pharmacological role of PrRP, and its underlying molecular mechanism, the invention provides compounds and related therapeutic methods for suppressing absence seizures in mammals. The compounds and therapeutic methods of the invention can thus be used in the therapy of epilepsies and other diseases associated with absence seizures. Additionally, the invention provides methods of rapidly screening for compounds that modulate AMPA receptor signaling and compounds that control absence seizures. The compounds so identified will be useful in the control of absence seizures, as well as in the prevention and treatment of conditions associated with tissues in which GPR10 is expressed, or in which known anti-epileptic drugs are effective.

In one aspect, the invention provides a method of controlling absence seizures. The method involves administering to a mammal susceptible to absence seizures an effective amount of PrRP or a functional analog thereof. As used herein, the term "mammal susceptible to absence seizures," refers to a human, veterinary animal or laboratory animal (e.g. non-human primate, rodent, feline or canine) that exhibits, can be induced to exhibit, or is at high risk of developing, absence seizures.

Absence seizures are brief attacks of impaired consciousness that can be distinguished from other forms of seizures both by their distinct electroencephalographic (EEG) patterns and by their response to pharmacological agents. By EEG, absence seizures are associated with bilateral synchronous and regular spike and wave discharges (SWD) with a frequency of 2.5 to 4 c/s, which start and end abruptly. Pharmacologically, absence seizures generally respond to the drugs ethosuximade, valproate and trimethadione, but are worsened by anti-convulsants such as carbamazepine and phenytoine which are effective in treating convulsive seizures.

In humans, several clinically recognized epilepsy syndromes, including childhood absence epilepsy, juvenile absence epilepsy, juvenile myoclonic epilepsy, myoclonic absence epilepsy, and eyelid myoclonia with absences, are associated with absence seizures. Epileptic syndromes are commonly classified according to the International Classification of Epileptic Syndromes proposed by the International League against Epilepsy in 1989.

Epidemiological studies have identified several predictive factors for the development of absence seizures, including past history of either febrile convulsions or generalized tonic-clonic seizures (GTCS), and family history of epilepsy or febrile convulsions (see, for example, Covanis et al., *Seizure* 1:281–289 (1992)). Because of the clear genetic predisposition for absence epilepsies, those skilled in the art understand that it will also be possible to determine susceptibility to absence seizures by genetic or biochemical profile.

Accordingly, a human "susceptible to absence seizures," can be a human exhibiting absence seizures, such as a human diagnosed with an epilepsy syndrome characterized by absence seizures, or a human considered to be at high risk of developing absence seizures.

A variety of non-human mammals that exhibit, or can be induced to exhibit, behavioral, electrographic and pharmacological characteristics of absence seizures in humans are known in the art. Such mammals are also considered herein to be "mammals susceptible to absence seizures." For example, Genetic Absence Epilepsy Rats from Strasbourg, or GAERS, exhibit behavioral and EEG patterns during spike and wave discharges (SWD) that are similar to those observed in humans during absence seizures (see Danober et al., *Prog. Neurobiol.* 55:27–57 (1998)). Other genetic models of absence epilepsy include the lethargic (lh/lh) mutant mouse (see Hosford et al., *Epilepsia* 38:408–414 (1997)), the WAG/Rij strain of rats (see Coenan et al., *Epilepsy Res.* 12:75–86 (1992)), and the tremor (tm/tm) mutant rat (Hanaya et al., *Epilepsia* 36:938–942 (1995)), which have been successfully used to predict or confirm the effects of a variety of anti-epileptic drugs in controlling absence seizures in humans.

Other relevant mammalian models of absence seizures in humans include pharmacological models, in which absence seizures are induced in laboratory animals, such as rodents, cats and primates, by administration of pentylenetetrazol, penicillin, gamma-hydroxybutyrate or GABA agonists (for a review, see Snead, *Epilepsia* 29:361–368 (1988)). Additionally, absence seizures can be induced in primates by thalamic stimulation (see, for example, David et al., *J. Pharmacol. Methods* 7:219–229 (1982)).

As used herein, the term "controlling," in relation to absence seizures, refers to a reduction in the frequency, duration, number or intensity of absence seizures in a treated mammal, as compared with the frequency, duration, number or intensity of absence seizures expected or observed without treatment. A determination of whether absence seizures are "controlled" by treatment can be made, for example, by direct observation, by self-reporting, or by examining on an EEG readout the frequency, duration, number or intensity or duration of spike and wave discharges (SWD)(see, for example, Example IV, below).

An amount of a pharmaceutical composition effective to control absence seizures is an amount effective to reduce the determined parameter (e.g. frequency, duration, number or intensity of absence seizures or SWD) by at least 10%. Preferably, the determined parameter will be reduced by at least 20%, more preferably at least 50%, such as at least 80%, in at least some treated mammals. Accordingly, a treatment that controls absence seizures will be useful in improving the quality of life in the treated mammals. Further description of effective amounts, formulations and routes of administration of the pharmaceutical compositions useful in the methods of the invention is provided below.

PrRP was originally identified as a peptide having the physiological role of promoting the release of prolactin, a hormone involved in mammary development and lactation, from the anterior pituitary (Hinuma et al., *Nature* 393:272–276 (1998)). As used herein, the term "PrRP" refers to a peptide having identity with at least 5 residues of the native sequence of a mammalian prolactin-releasing peptide (PrRP), and which binds a "PrRP receptor" with an affinity (Kd) of about $10^{-5}$ M or less. A PrRP of the invention can thus have identity with at least 5, 6, 7, 8, 9, 10, 15, 20 or more contiguous or non-contiguous amino acid residues of a native PrRP. Preferably, a PrRP of the invention binds a PrRP receptor with a Kd of about $10^{-6}$ M or less, more preferably about $10^{-7}$ M or less, most preferably about $10^{-8}$ M or less, including about $10^{-9}$ M or less, such as $10^{-10}$ M or less.

Mature, native PrRP peptides exist in at least two forms, a 31 amino acid peptide (PrRP-31) and a 20 amino acid peptide (PrRP-20), which are amidated at the carboxy-terminus. PrRP-31 and PrRP-20 are derived from a longer preproprotein. The purification of PrRP-31 and PrRP-20 from bovine hypothalamus, the cloning of PrRP prepro-protein from bovine, rat and human, the characterization of PrRP-31 and PrRP-20 as peptides having prolactin-releasing activity towards rat anterior pituitary cells in vitro, and the importance of the C-terminal amide for PrRP activity, are described in Hinuma et al., *Nature* 393:272–276 (1998).

The amino acid sequences of PrRP-31 from bovine, rat and human are as follows:

Bovine: SRAHQHSNEIRTPDINPAWYAGRGIRPVGRF (SEQ ID NO:13)
Rat: SRAHQHSMETRTPDINPAWYTGRGIRPVGRF (SEQ ID NO:14)
Human: SRTHRHSMEIRTPDINPAWYASRGIRPVGRF (SEQ ID NO:15)

The amino acid sequences of PrRP-20 from bovine, rat and human, which contain the C-terminal 20 amino acids of PrRP-31, are as follows:

Bovine: TPDINPAWYAGRGIRPVGRF (SEQ ID NO:16)
Rat: TPDINPAWYTGRGIRPVGRF (SEQ ID NO:17)
Human: TPDINPAWYASRGIRPVGRF (SEQ ID NO:18)

The term "PrRP" is intended to encompass PrRP-31 and PrRP-20 from bovine, rat and human, having the amino acid sequences shown above, as well as PrRP-31 and PrRP-20 from other mammalian species, including, for example, non-human primates, mouse, rabbit, porcine, ovine, canine and feline species. The sequences of PrRP from other mammalian species can be readily determined by those skilled in the art, for example either by purifying PrRP from hypothalamic extracts, or by cloning PrRP preproproteins, following the methods described in Hinuma et al., *Nature* 393:272–276 (1998). Because of the high degree of identity between bovine, rat and human sequences, it is expected that PrRP from other mammalian species will be substantially similar in structure and function to the known PrRP sequences.

The term "PrRP" is also intended to encompass peptides that are longer or shorter than PrRP-31 or PrRP-20, so long as they have identity with at least 5 residues of the native sequence of a mammalian prolactin-releasing peptide (PrRP), and can bind the PrRP receptor GPR10 with an affinity (Kd) of less than about $10^{-5}$ M. Thus, the term "PrRP" encompasses peptides that have one or several amino acid additions or deletions compared with the amino acid sequence of a PrRP-31 or PrRP-20. Those skilled in the art recognize that such modifications can be desirable in order to enhance the bioactivity, bioavailability or stability of the PrRP, or to facilitate its synthesis or purification.

The term "PrRP" is further intended to encompass peptides having identity with at least 5 residues of the native sequence of a mammalian prolactin-releasing peptide (PrRP), which bind a PrRP receptor with an affinity (Kd) of about $10^{-5}$ M or less, and which have one or several minor modifications to the native PrRP sequence. Contemplated modifications include chemical or enzymatic modifications (e.g. acylation, phosphorylation, glycosylation, etc.), and substitutions of one or several amino acids to a native PrRP sequence. Those skilled in the art recognize that such modifications can be desirable in order to enhance the bioactivity, bioavailability or stability of the PrRP, or to facilitate its synthesis or purification.

Contemplated amino acid substitutions to the native sequence of a PrRP include conservative changes, wherein a substituted amino acid has similar structural or chemical properties (e.g., replacement of an apolar amino acid with another apolar amino acid; replacement of a charged amino acid with a similarly charged amino acid, etc.). Those skilled in the art also recognize that nonconservative changes (e.g., replacement of an uncharged polar amino acid with an apolar amino acid; replacement of a charged amino acid with an uncharged polar amino acid, etc.) can be made without affecting the function of PrRP. Furthermore, non-linear variants of a PrRP sequence, including branched sequences and cyclic sequences, and variants that contain one or more D-amino acid residues in place of their L-amino acid counterparts, can be made without affecting the function of PrRP.

In particular, the term "PrRP" is intended to encompass peptides having minor modifications to the native PrRP sequence that serve to increase its penetration through the blood-brain barrier (BBB). For a review of strategies for increasing bioavailability of peptides and peptide drugs in the brain, and of methods for determining the permeability of peptides through the BBB using in vitro and in vivo assays, see Engleton et al., *Peptides* 9:1431–1439 (1997).

Strategies that have been successfully used to increase the permeability of other neuropeptides through the BBB are particularly contemplated. For example, modifying the opioid peptide analgesic Met-enkephalin with D-penicillamine at two positions, forming a disulfide bridge that conformationally constrains the peptide, dramatically increases its stability towards BBB endothelial cell proteases and its BBB permeability. Likewise, linking two enkephalin peptides, each containing a D-amino acid residue at the second position, with a hydrazide bridge, results in a metabolically stable peptide with improved brain penetration. Additionally, halogenation of an enkephalin peptide has been shown to increase its BBB permeability. Similar modifications to PrRP peptides are likewise expected to be advantageous.

Additional modifications to a PrRP peptide that can increase its BBB penetration include conjugating the peptide to a lipophilic moiety, such as a lipophilic amino acid or methyldihydropyridine. PrRP peptide can also be conjugated to a transporter, such as the monoclonal antibody OX26 which recognizes the transferrin receptor, or cationized albumin which utilizes the adsorptive mediated endocytosis pathway, so as to increase its BBB penetration.

Those skilled in the art can determine which residues and which regions of a native PrRP sequence are likely to be tolerant of modification and still retain the ability to bind PrRP receptor with high affinity. For example, amino acid substitutions, or chemical or enzymatic modifications, at residues that are less well conserved between species are more likely to be tolerated than substitutions at highly conserved residues. Accordingly, an alignment can be performed among PrRP sequences of various species to determine residues and regions in which modifications are likely to be tolerated.

Additional guidance for determining residues and regions of PrRP likely to be tolerant of modification is provided by studies of PrRP fragments and variants. For example, based on the observation that PrRP-20 has similar ability to transduce signals through the PrRP receptor as PrRP-31 (see, for example, Hinuma et al., *Nature* 393:272–276 (1998)), it is likely that the N-terminus of PrRP is highly tolerant of the modifications described herein.

In particular, as described in Roland et al., *Endocrinology* 140:5736–5745 (1999), a peptide designated PrRP(25–31), consisting of the C-terminal seven amino acids of PrRP (IRPVGRF, SEQ ID NO:23) binds GPR10 with an apparent affinity of 200 nM, compared with an affinity of about 1 nM for PrRP-31 or PrRP-20, and mobilizes calcium in CHOK1 cells transfected with GPR10. Thus, a peptide consisting of, or comprising, the amino acid sequence designated SEQ ID NO:23 is encompassed by the term "PrRP."

Alanine scanning mutagenesis of PrRP(25–31) indicates that variants with substitutions of Ile25, Pro27, Val28, or Phe31 retain the ability to bind GPR10 with an affinity of about $10^{-6}$ M. Thus, a PrRP can consist of, or comprise, the amino acid sequences XRPVGRF (SEQ ID NO:19), IRX-VGRF (SEQ ID NO:20), IRPXGRF (SEQ ID NO:21), IRPVGRX (SEQ ID NO:22), where "X" is any amino acid, preferably a non-polar amino acid, more preferably alanine. Substitutions of Arg26 or Gly29 were shown to substantially reduce binding affinity of PrRP(25–31) for GPR10, and substitution of Arg30 completely eliminated binding. Substitution of either Arg26 or Arg30 with lysine or citrulline also completely eliminated binding. More generally, a PrRP peptide can be considered to consist of, or comprise, the amino acid sequence XRXXGRX, so long as it retains PrRP receptor binding activity.

In the modified PrRP sequences described above, the effect of amino acid substitutions on calcium signaling was commensurate with the effect on binding to GPR10 (see Roland et al., *Endocrinology* 140:5736–5745 (1999)). Accordingly, in view of the disclosure herein, it is predictable that a peptide considered to be a "PrRP" by GPR10 binding criteria will also be functionally active in mediating G-protein coupled signaling through PrRP receptor, inhibiting AMPA mediated signaling in whole cell preparations, inhibiting oscillatory activity in RTN preparations, suppressing absence seizures in susceptible mammals, and preventing or treating neurological and psychiatric disorders in which PrRP-31 or PrRP-20 are effective. Thus, as described further below, a peptide having a modified PrRP sequence can be assayed by any of these functional criteria to confirm that it is a PrRP.

The PrRP peptides of the invention can be prepared in substantially purified form using either conventional peptide synthetic methods (see, for example, Roland et al., *Endocrinology* 140:5736–5745 (1999)), or using conventional biochemical purification methods, starting either from tissues containing PrRP or from recombinant sources (see, for example, Hinuma et al., *Nature* 393:272–276 (1998)).

In methods of controlling absence seizures, and for certain other therapeutic applications, it may be preferable to use a PrRP functional analog rather than a PrRP peptide. For example, a PrRP functional analog can be more stable, more active, or have higher inherent ability to penetrate the BBB than a PrRP. As used herein, the term "PrRP functional analog" refers to a molecule that binds the PrRP receptor GPR10 with an affinity (Kd) of about $10^{-5}$ M or less, and which is not encompassed within the definition of a "PrRP," as set forth above. Preferably, a PrRP functional analog will bind a PrRP receptor with a Kd of about $10^{-5}$ M or less, more preferably about $10^{-9}$ M or less, most preferably about $10^{-10}$ M or less, including about $10^{-9}$ M or less, such as about $10^{-10}$ M or less.

The invention thus provides PrRP functional analogs. The PrRP functional analogs of the invention will generally act as PrRP receptor agonists, and thus be able to mediate the same biochemical and pharmacological effects (e.g. signal transduction through the PrRP receptor, reduction of AMPA receptor activity, suppression of absence seizures in mammals) as PrRP. However, a PrRP functional analog identified by the methods described herein can alternatively act as a PrRP receptor antagonist, and thus inhibit signaling through GPR10, prevent the suppression of AMPA receptor mediated activity, or both. Such antagonists can advantageously be used in therapeutic applications where a reduction in PrRP receptor signaling is desired, including in the treatment of sleep and attention disorders. PrRP functional analogs of the invention, which are themselves not appropriate for therapeutic use, can advantageously be used to optimize the design of effective therapeutic compounds, or used in the screening methods described herein as competitors.

A PrRP functional analog can be a naturally occurring macromolecule, such as a peptide, nucleic acid, carbohydrate, lipid, or any combination thereof. A PrRP functional analog also can be a partially or completely synthetic derivative, analog or mimetic of such a macromolecule, or a small organic or inorganic molecule prepared partly or completely by synthetic chemistry methods. A PrRP functional analog can be identified starting either by rational design based on the corresponding peptide, by functional screening assays, or by a combination of these methods.

PrRP functional analogs include peptidomimetics of PrRP, such as peptidomimetics of a peptide containing, or consisting of, the amino acid sequence set forth as SEQ ID NO:23. As used herein, the term "peptidomimetic" refers to a non-peptide agent that is a topological analog of the corresponding peptide. Those skilled in the art understand that the identified ability of PrRP-31, PrRP-20, PrRP(25–31) and of certain single amino acid variants of PrRP(25–31) to bind PrRP receptor with high affinity, provides sufficient structural and functional information to rationally design peptidomimetics of PrRP.

Such a peptidomimetic can, for example, retain some or all of the functional groups of the amino acids shown to be functionally important in the C-terminus of PrRP (such as the 3-guanylpropyl radical of Arg26 and Arg30, the hydrogen of Gly29, etc.). A peptidomimetic of PrRP can also, for example, consist partially or completely of a non-peptide backbone used in the art in the design of other peptidomimetics, such as a glucose scaffold, a pyrrolidinone scaffold, a steroidal scaffold, a benzodiazepine scaffold, or the like.

Methods of rationally designing peptidomimetics of peptides, including neuropeptides, are known in the art. For example, the rational design of three peptidomimetics based on the sulfated 8-mer peptide CCK26-33, and of two peptidomimetics based on the 11-mer peptide Substance P, and related peptidomimetic design principles, are described in Horwell, *Trends Biotechnol.* 13:132–134 (1995).

Individual, rationally designed peptidomimetics of PrRP peptides can be assayed for their ability to bind the PrRP receptor, or to induce signaling through the PrRP receptor, or both, using one or more of the assays described herein. Similarly, a plurality of peptidomimetic compounds, such as variants of a peptidomimetic lead compound, or a plurality of other compounds, can be assayed simultaneously or sequentially using the binding, signaling and pharmacological assays described herein.

A candidate compound can be assayed to determine whether it is a PrRP or PrRP functional analog either by a signaling assay, a binding assay, or both. The number of different compounds to screen in a particular assay can be determined by those skilled in the art, and can be 2 or more, such as 5, 10, 15, 20, 50 or 100 or more different compounds. For certain applications, such as when a library of random compounds is to be screened, and for automated procedures, it may be desirable to screen $10^3$ or more compounds, such as $10^5$ or more compounds, including $10^7$ or more compounds.

Methods for producing large libraries of chemical compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422–428 (1998); Tietze et al., *Curr. Biol.*, 2:363–371 (1998); Sofia, *Mol. Divers.* 3:75–94 (1998); Eichler et al., *Med. Res. Rev.* 15:481–496 (1995); and the like. Libraries containing large numbers of natural and synthetic compounds also can be obtained from commercial sources.

In one embodiment, a signaling assay can be performed to determine whether a candidate compound is a PrRP or a PrRP functional analog. In such an assay, a PrRP receptor is contacted with one or more candidate compounds under conditions wherein the PrRP receptor produces a predetermined signal in response to PrRP, and a compound is identified that alters production of the predetermined signal. The candidate compound can be tested at a range of concentrations to establish the concentration where half-maximal signaling occurs; such a concentration is generally similar to the dissociation constant (Kd) for PrRP receptor binding.

As used herein, the term "PrRP receptor," is intended to refer to a mammalian seven-transmembrane-domain G-protein coupled receptor, variously designated in the art "GPR10" (Marchese et al., *Genomics* 29:335–344 (1995)), "hGR3" (Hinuma et al., Nature 393:272–276 (1998)) or "UHR-1" (Welch et al., *Biochem. Biophys. Res. Commun.* 209:606–613 (1995)). A "PrRP receptor" can have minor modifications to the native mammalian sequence, so long as the minor modifications do not significantly alter its ability to bind PrRP, interact with AMPA receptor associated molecules, signal through a G-protein coupled signal transduction pathway, or modulate AMPA receptor signaling, depending on the particular application of the PrRP receptor in the methods of the invention.

The PrRP receptor to be contacted in the methods of the invention can be naturally expressed in a tissue, cell or extract. Alternatively, where it is desired to increase the PrRP receptor concentration, or to express PrRP receptor in host cells where it is not normally expressed, including mammalian, yeast and bacterial cells, the PrRP receptor can be recombinantly expressed. Methods of recombinantly expressing PrRP receptor, either transiently or stably, in a variety of host cells, are well known in the art (see, for example, Hinuma et al., *Nature* 393:272–276 (1998) and Roland et al., *Endocrinology* 140:5736–5745 (1999)).

As used herein, the term "predetermined signal" refers to a readout, detectable by any analytical means, that is a qualitative or quantitative indication of activation of G protein-dependent signal transduction through PrRP receptor. The term "G protein" refers to a class of heterotrimeric GTP binding proteins, with subunits designated Gα, Gβ and Gγ, that couple to seven-transmembrane cell surface receptors to transduce a variety of extracellular stimuli, including light, neurotransmitters, hormones and odorants to various intracellular effector proteins. G proteins are present in both eukaryotic and prokaryotic organisms, including mammals, other vertebrates, Drosophila and yeast.

As described in Hinuma et al., *Nature* 393:272–276 (1998), contacting PrRP receptor with PrRP leads to activation of arachidonic acid metabolite release in mammalian cells recombinantly expressing PrRP receptor. Therefore, an exemplary predetermined signal that is a qualitative or quantitative indication of activation of G protein-dependent signal transduction through PrRP receptor is arachadonic acid metabolite release. Similarly, as described in Roland et al., *Endocrinology* 140:5736–5745 (1999), contacting PrRP receptor with PrRP leads to calcium mobilization in mammalian cells recombinantly expressing PrRP receptor, which can be measured, for example, using the calcium indicator fluo-3 and a fluorescence monitoring system.

If desired, a predetermined signal other than arachidonic acid metabolite release or $Ca^{2+}$ influx can be used as the readout in the methods of the invention. The specificity of a G protein for cell-surface receptors is determined by the C-terminal five amino acids of the Gα subunit. The nucleotide sequences and signal transduction pathways of different classes and subclasses of Gα subunits in a variety of eukaryotic and prokaryotic organisms are well known in the art. Thus, any convenient G-protein mediated signal transduction pathway can be assayed by preparing a chimeric Gα containing the C-terminal residues of a Gα that couples to PrRP receptor, such as Gαq, with the remainder of the protein corresponding to a Gα that couples to the signal transduction pathway it is desired to assay.

Methods of recombinantly expressing chimeric Gα proteins, and their use in G-protein signaling assays, are known in the art and are described, for example, in and Saito et al., *Nature* 400:265–269 (1999), and Coward et al., *Anal. Biochem.* 270:2424–248 (1999)).

Signaling through G proteins can lead to increased or decreased production or liberation of second messengers, including, for example, arachidonic acid, acetylcholine, diacylglycerol, cGMP, cAMP, inositol phosphate and ions; altered cell membrane potential; GTP hydrolysis; influx or efflux of amino acids; increased or decreased phosphorylation of intracellular proteins; or activation of transcription. Thus, by using a chimeric Gα subunit that binds PrRP receptor and couples to a desired signal transduction pathway in the methods of the invention, those skilled in the art can assay any convenient G protein mediated predetermined signal in response to PrRP and PrRP functional analogs.

Various assays, including high throughput automated screening assays, to identify alterations in G protein coupled signal transduction pathways are well known in the art. Various screening assay that measure $Ca^{++}$, cAMP, voltage changes and gene expression are reviewed, for example, in Gonzalez et al., *Curr. Opin. in Biotech.* 9:624–631 (1998); Jayawickreme et al., *Curr. Opin. Biotech.* 8:629–634 (1997); and Coward et al., *Anal. Biochem.* 270:2424–248 (1999). Yeast cell-based bioassays for high-throughput screening of drug targets for G protein coupled receptors are described, for example, in Pausch, *Trends in Biotech.* 15:487–494 (1997). A variety of cell-based expression systems, including bacterial, yeast, baculovirus/insect systems and mammalian cells, useful for detecting G protein coupled receptor agonists and antagonists are reviewed, for example, in Tate et al., *Trends in Biotech.* 14:426–430 (1996).

Assays to detect and measure G protein-coupled signal transduction can involve first contacting the isolated cell or membrane with a detectable indicator. A detectable indicator can be any molecule that exhibits a detectable difference in a physical or chemical property in the presence of the substance being measured, such as a color change. Calcium indicators, pH indicators, and metal ion indicators, and assays for using these indicators to detect and measure selected signal transduction pathways are described, for example, in Haugland, *Molecular Probes Handbook of Fluorescent Probes and Research Chemicals*, Sets 20–23 and 25 (1992–94). For example, calcium indicators and their use are well known in the art, and include compounds like Fluo-3 AM, Fura-2, Indo-1, FURA RED, CALCIUM GREEN, CALCIUM ORANGE, CALCIUM CRIMSON, BTC, OREGON GREEN BAPTA, which are available from Molecular Probes, Inc., Eugene Oreg., and described, for example, in U.S. Pat. Nos. 5,453,517, 5,501,980 and 4,849,362.

Assays to determine changes in gene expression in response to a PrRP or PrRP functional analog can involve first transducing cells with a promoter-reporter nucleic acid construct such that a protein such as β-lactamase, luciferase, green fluorescent protein or β-galactosidase will be expressed in response to contacting PrRP receptor with a PrRP or PrRP functional analog. Such assays and reporter systems are well known in the art.

An assay to determine whether a candidate compound is a PrRP or a PrRP functional analog is performed under conditions in which contacting the receptor with a known PrRP, such as PrRP-31 or PrRP-20, would produce a predetermined signal. If desired, the assay can be performed in the presence of a known PrRP. Preferably, the PrRP concentration will be within 10-fold of the $EC_{50}$. Thus, an agonist that competes with PrRP for signaling through the PrRP receptor, or indirectly potentiates the signaling activity of PrRP, can be readily identified. Likewise, an antagonist that prevents PrRP from binding the PrRP receptor, or indirectly decreases the signaling activity of PrRP, can also be identified.

As described in Example II, below, functional interaction of PrRP with GPR10 results in the association of GPR10 through its C-terminus with AMPA receptor associated molecules. Thus, a further signaling assay for identifying a PrRP or PrRP functional analog consists of contacting a PrRP receptor with a candidate compound under conditions wherein PrRP promotes interaction of PrRP receptor with an AMPA receptor associated protein, and determining the ability of the candidate compound to promote the interaction of the PrRP receptor with the AMPA receptor associated protein. A candidate compound that promotes the interaction of PrRP receptor with an AMPA receptor associated protein is characterized as a PrRP or PrRP functional analog.

Exemplary AMPA receptor associated molecules include PICK1 (see Xia et al., *Neuron* 22:179–187 (1999)), GRIP1 (Dong et al., *J. Neurosci.* 19:6930–6941 (1999)), and GRIP2/ABP (Dong et al., *J. Neurosci.* 19:6930–6941 (1999); Srivista et al., *Neuron* 21:581–591 (1998)), which are PDZ domain containing proteins, and other proteins that similarly interact with the GluR2 or GluR3 subunits of AMPA receptors.

Methods of determining the interaction between PrRP receptor and an AMPA receptor associated protein, and suitable compositions for practicing the methods, are described in Example II, below. For example, a cell, such as a mammalian, yeast or bacterial cell, can be cotransfected with a nucleic acid expression construct directing the expression of PrRP receptor, and a nucleic acid molecule expression construct directing the expression of AMPA receptor associated protein, and the cell contacted with a candidate compound. Interaction between the PrRP receptor and AMPA receptor associated protein following such contacting can be determined, for example, by co-immunoprecipitation of the two proteins, or by intracellular or surface clustering of the two proteins. Nucleic acid expression constructs and suitable host cells for expressing PrRP receptor and AMPA receptor associated proteins, and immunological reagents and methods suitable for detecting such interactions, are known in the art.

A candidate compound can alternatively or additionally be assayed to determine whether it is a PrRP or PrRP functional analog by a PrRP receptor binding assay. If desired, a binding assay can be followed by a signaling assay, to determine whether the identified compound is a PrRP receptor agonist or antagonist. Receptor binding assays, including high-throughput automated binding assays, are well known in the art, and any suitable direct or competitive binding assay can be used. Exemplary high-throughput receptor binding assays are described, for example, in Mellentin-Micelotti et al., *Anal. Biochem.* 272:P182–190 (1999); Zuck et al., *Proc. Natl. Acad. Sci. USA* 96:11122–11127 (1999); and Zhang et al., *Anal. Biochem.* 268;134–142 (1999.). The assay format can employ a cell, cell membrane, or artificial membrane system, so long as the PrRP receptor is in a suitable conformation for binding PrRP with a similarly affinity and specificity as a PrRP receptor expressed on the surface of a mammalian cell.

Contemplated binding assays can involve detectably labeling a candidate compound, or competing an unlabeled candidate compound with a detectably labeled PrRP. A detectable label can be, for example, a radioisotope, fluorochrome, ferromagnetic substance, or luminescent substance. Exemplary radiolabels useful for labeling compounds include $^{125}I$, $^{14}C$ and $^3H$. Methods of detectably labeling organic molecules, either by incorporating labeled amino acids into the compound during synthesis, or by derivatizing the compound after synthesis, are known in the art.

In the binding and signaling assays described above, appropriate conditions for determining whether a compound is a PrRP or PrRP functional analog are those in which a control PrRP exhibits the binding or signaling property. The control assay can be performed before, after or simultaneously with the test assay.

The invention also provides methods of identifying compounds that modulate AMPA receptor signaling, including compounds that suppress AMPA receptor signaling and compounds that enhance AMPA receptor signaling. Such compounds can be used, for example, as therapeutic compounds for controlling absence seizures, as well as in the prevention and treatment of conditions associated with tissues in which GPR10 is expressed. Such compounds can also be used, for example, in the design and development of compounds which themselves can be used as therapeutics, or for further analysis of biochemical pathways.

The method consists of providing one or more compounds that are PrRPs or PrRP functional analogs, and determining the ability of the compound to modulate AMPA receptor signaling. The one or more compounds that are PrRPs or PrRP functional analogs can be identified, isolated or prepared by the methods and criteria set forth above.

Assays for determining AMPA receptor signaling can either directly measure AMPA receptor electrophysiological activity in a cell or tissue, or measure a biochemical or physiological property that is correlated with AMPA receptor activity. Appropriate assays and conditions for determining whether a compound modulates AMPA receptor signaling are those in which a control PrRP modulates AMPA receptor signaling. The control assay can be performed before, after or simultaneously with the test assay, depending on the particular assay. Such assays are known in the art or described herein, and include both manual and high-throughput automated assays.

A method of determining whether a PrRP or PrRP functional analog modulates AMPA receptor electrophysiological activity can involve determining AMPA receptor-mediated oscillatory activity in a tissue, such as a neural tissue, that expresses both PrRP receptors and AMPA receptors. Example III, below, describes exemplary conditions for determining AMPA receptor-driven oscillatory activity in a thalamic preparation. Application of PrRP reduced AMPA receptor mediated oscillatory activity, in a dose-dependent manner. Accordingly, an assay of thalamic oscillatory activity can be used to determine whether a compound modulates AMPA receptor signaling.

A further method of determining whether a PrRP or PrRP functional analog modulates AMPA receptor electrophysiological activity can involve an assay of the electrophysiological properties of a single cell or cell population which normally expresses (e.g. RTN neurons), or which recombinantly expresses, functional PrRP receptors and AMPA receptors. Methods of transiently or stably transfecting cells with AMPA receptors are well known in the art and are described, for example, in Hall et al., *J. Neurochem.* 68:625–630 (1997), and in Hennegriff et al., *J. Neurochem.* 68:2424–2434 (1997).

Example 5, below, and Smith et al., *J. Neuroscience* 20:2073–2085 (2000), describe exemplary conditions for determining AMPA receptor mediated electrophysiological recordings from whole cells. In brief, the method involves detecting AMPA receptor mediated currents using whole cell patch clamp recordings in the presence of an AMPA agonist. The modulatory effect of a test compound on the AMPA receptor mediated currents can thus be determined. Such assays can be performed in the presence of a drug such as cyclothiazide to reduce AMPA receptor densensitization.

Alternatively, or additionally, a method of determining whether a PrRP or PrRP functional analog modulates AMPA receptor signaling activity can involve an assay of AMPA receptor-mediated second messenger responses in cells expressing functional PrRP receptors and AMPA receptors. Such assays are advantageous in that they are readily amenable to automation, using methods known in the art, allowing rapid and high-throughput screening of compounds.

Example 6, below, describes exemplary conditions for determining AMPA receptor mediated calcium ion or sodium ion influx into cells in response to a compound that modulates AMPA receptor signaling. In brief, the method involves detecting AMPA receptor mediated ion influx using fluorescent ion indicators and either microscopic visualization, or an automated fluorometric imaging plate reader (FLIPR). The modulatory effect of a test compound on AMPA receptor mediated ion influx can thus be determined.

The invention also provides methods of identifying compounds for controlling absence seizures. The method consists of providing a compound that is a PrRP or PrRP functional analog, and determining the ability of the compound to control absence seizures in a mammal. Optionally, the compound can be a compound determined to suppress AMPA receptor mediated-signaling by any of the assays described herein.

Assays for determining whether a compound controls absence seizures in a mammal are known in the art. For example, as described in Example IV, below, absence seizure activity can be determined in a mammalian model of absence epilepsy, the GAERS, in which spontaneous spike-and-wake discharges are evidenced by EEG recordings. Administration of PrRP decreased seizure activity in the GAERS, in a dose-dependent manner. Accordingly, an in vivo assay in a mammal susceptible to absence seizures, including a rodent, non-human primate, or human, can be used to identify a compound for controlling absence seizures.

It is expected that the PrRP and PrRP functional analog compounds and therapeutic compositions of the invention will have beneficial activities apart from, or in addition to, controlling absence seizures. As described herein, high levels of GPR10 expression have been observed in a number of discrete locations in the brain and peripheral tissues (see Example I and Table 2). In particular, GPR10 is expressed at high levels in the GABAergic neurons of the RTN. The GABAergic neurons of the RTN change their firing patterns in response to sleep and wake states. During periods of EEG-synchronized, deep sleep, RTN neurons generate rhythmic, high-frequency bursts of action potentials, while during waking and REM sleep, these neurons generate sequences of tonic action potential activity (for a review, see McCormick et al., Annu. Rev. Neurosci., 20:185–215 (1997)). Accordingly, it is contemplated that PrRP and PrRP functional analogs, including functional analogs that act as antagonists of the PrRP receptor, will be effective in preventing or ameliorating sleep disorders and attention disorders by modulating signaling through the GABAergic neurons of the RTN. Attention disorders are well known in the art and include, for example, attention deficit hyperactivity disorder, affective disorders, and disorders of memory.

A variety of sleep disorders are also well known in the art and are described, for example, in Diagnostic and Statistical Manual of Mental Disorders, 4th Edition (1994), published by the American Psychiatric Association. The most common sleep disorder is primary insomnia, or a difficulty in initiating or maintaining sleep, which affects a large percentage of the population at some point in their lives. Other common sleep disorders include hypersomnia, or excessive daytime sleepiness, narcolepsy, which is characterized by sudden and irresistible bouts of sleep, and sleep apnea, which is a temporary cessation of breathing during sleep.

As described herein, GPR10 is also expressed in the Area Postrema (AP), Bed nucleus stria terminalis (BST), Central nucleus amygdala (CeA), hypothalamic. nucleus (Hypo), Superior colliculus (SC), and Shell, nucleus accumbens (SNAc) of the brain, as well as in peripheral tissues including the Adrenal medulla (AdM) and uterus. Accordingly, it is contemplated that PrRP and PrRP functional analogs, including analogs that act as antagonists of the PrRP receptor, will be effective in preventing, ameliorating or modulating conditions associated with these regions of the brain and periphery, as shown in Table 1, below.

TABLE 1

THERAPEUTIC POTENTIAL OF PrRP

| Therapeutic Potential | GPR10 Localization |
|---|---|
| Stress-induced anorexia | Hypo, BST, CeA |
| Stress-induced hypertensive crisis | NTS, AP |
| Anxiety | BST, CeA, Hypo |
| Excessive fear response | CeA |
| Posttraumatic Stress disorder | BST, CeA, Hypo, AP |
| Nicotine induced cardiac arrhythmias | NTS, AP |
| Nicotine induced coronary spasms | NTS, AP |
| Pheochromocytoma | AdM |
| Insomnia | RTN |
| Excessive somnolence | RTN |
| Petit mal (absence) seizure | RTN |
| Visual processing and attention deficits | SC |
| Drug addiction | SNAc |
| Inducing labor | Uterus |
| Birth control | Uterus |

It is known in the art that currently available drugs for controlling absence seizures are effective in the prevention and treatment of a variety of neurologic and psychiatric conditions. For example, valproate, one of the most commonly used medications for controlling absence seizures, is also useful in the treatment of bipolar and schizoaffective disorders, depression, anxiety, alcohol withdrawal and dependence, agitation associated with dementia, impulsive aggression, neuropathic pain, and for the prophylactic treatment of migraine (see, for example, Loscher, Prog. Neurobiol. 58:31–59 (1999), and Davis et al., J. Clin. Psychopharmacol. 20:1S-17S (2000)). Thus, the PrRP and PTRP analogs and compositions of the invention can be used to treat conditions in which other anti-absence seizures drugs are effective.

The PrRP compounds and compositions of the invention can be formulated and administered by those skilled in the art in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for controlling absence seizures in humans can be extrapolated based on the activity of the compound in the assays described herein. An appropriate amount and formulation for use in humans for other indications can be extrapolated from credible animal models known in the art of the particular disorder.

The total amount of compound can be administered as a single dose or by infusion over a relatively short period of time, or can be administered in multiple doses administered over a more prolonged period of time. Additionally, the compounds can be administered in slow-release matrices, which can be implanted for systemic delivery or at the site of the target tissue. Contemplated matrices useful for controlled release of therapeutic compounds are well known in the art, and include materials such as DepoFoam™, biopolymers, micropumps, and the like.

The compounds and compositions of the invention can be administered to the subject by any number of routes known in the art including, for example, intravenously, intramuscularly, subcutaneously, intraorbitally, intracapsularly, intraperitoneally, intracisternally, intra-articularly, intracerebrally, orally, intravaginally, rectally, topically, intranasally, or transdermally. A preferred route for humans is oral administration.

PrRP or a PrRP functional analog can be administered to a subject as a pharmaceutical composition comprising the compound and a pharmaceutically acceptable carrier. Those skilled in the art understand that the choice of a pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters.

A pharmaceutically acceptable carrier can contain physiologically acceptable compounds that stabilize the compound, increase its solubility, or increase its absorption. Such physiologically acceptable compounds include carbohydrates such as glucose, sucrose or dextrans; antioxidants, such as ascorbic acid or glutathione; chelating agents; and low molecular weight proteins.

For applications that require the compounds and compositions to cross the blood-brain barrier, formulations that increase the lipophilicity of the compound are particularly desirable. For example, the compounds of the invention can be incorporated into liposomes (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer.

The compounds of the invention can also be prepared as nanoparticles. Adsorbing peptide compounds onto the surface of nanoparticles has proven effective in delivering peptide drugs to the brain (see Kreuter et al., *Brain Res.* 674:171–174 (1995)). Exemplary nanoparticles are colloidal polymer particles of poly-butylcyanoacrylate with PrRP adsorbed onto the surface and then coated with polysorbate 80.

In current absence seizure treatment regimes, more than one compound is often administered to an individual for maximal seizure control. Thus, for use in controlling absence seizures, PrRP and its functional analogs can advantageously be formulated with a second compound that controls absence seizures. Such compounds include, for example, valproate, ethosuximade, flunarizine, trimethadione and lamotrigine. Contemplated methods of controlling absence seizures include administering the compounds and compositions of the invention alone, in combination with, or in sequence with, such other compounds.

The following examples are intended to illustrate but not limit the present invention.

EXAMPLE I

Localization of GPR10 in the Rat Brain

This example shows the distribution of GPR10 mRNA in the brain, and particularly shows that GPR10 is highly expressed the GABAnergic neurons of the RTN.

Previous studies using Northern blot analysis have demonstrated that the receptor for PrRP, GPR10 is highly expressed in the pituitary, but absent in the brain. In order to determine the expression pattern of GPR10 in the brain, the more sensitive approach of in situ hybridization analysis was used.

In situ hybridization was performed essentially as described in Winzer-Serhan et al., *Brain Res. Brain Res. Protoc.* 3:229–241 (1999), and Winzer-Serhan et al., *J. Comp. Neural.* 386:540–554 (1997). Briefly, adult Sprague-Dawley rat brains were quickly removed and placed in methylbutane cooled to −20° C. for 1 minute. Twenty micron frozen sections were thaw-mounted onto poly-L-lysine coated glass slides, fixed in 4% paraformaldehyde in 0.1 M PBS pH 7.4, dessicated and stored at −20° C. until prehybridization. Pretreated sections were incubated overnight at 60° C. in hybridization buffer (50% formamide, 10% dextran sulfate, 500 μg/ml tRNA, 10 mM DTT, 0.3 M NaCl, 10 mM Tris pH 8.0, 1 mM EDTA pH 8.0) with $^{35}$S-labeled GPR10 sense and antisense cRNA probes ($10^7$ cpm/ml). Sections were washed, dehydrated in graded ethanol, and opposed to B-max film with $^{14}$C standards of known radioactivity. Slides were dipped in liquid Kodak NT2B emulsion and exposed for 4 weeks at 4° C. Developed sections were cresyl violet stained, coverslipped, and viewed under dark field microscopy. Adjacent sections were also labeled with S35-labeled sense GPR10 cRNA as control. The control sections showed no specific staining.

Figure 1B:
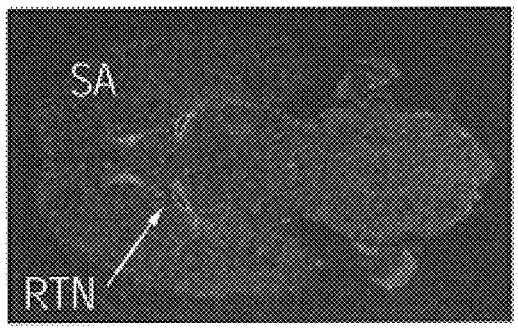

By in situ hybridization analysis, GPR10 was shown to be prominently expressed in the reticular thalamic nucleus (RTN), as well as in a few other discrete locations of the forebrain, midbrain and brainstem, as shown in FIGS. 1A and 1B and Table 2. In situ hybridization analysis of GPR10 expression has also been presented in Roland et al., *Endocrinology* 140:5736–5745 (1999).

By Northern blot (NB) analysis of a human tissue mRNA blot (obtained from Clontech), GPR10 was also shown to be expressed in the uterus.

TABLE 2

| GPR10 CENTRAL AND PERIPHERAL DISTRIBUTION | |
|---|---|
| Forebrain | |
| Shell accumbens | + + |
| Cortex | + |
| Lateral septal nucleus | + + |
| Ventricular/Ependymal lining | + + |
| Bed nucleus stria terminalis | + |
| Medial preoptic area | + + |
| Medial preoptic nucleus | + + + |
| Paraventricular nucleus, parvicellular division, hypothalamus | + + + |
| Periventricular nucleus, hypothalamus | + + + |
| Ventrolateral hypothalamus | + + |
| Lateral hypothalamus | + |
| Ventomedial hypothalamus | + |
| Lateral hypothalamus | + |
| Central nucleus, amygdala | + + |
| Reticular thalamic nucleus | + + + + |
| Dorsal premammillary nucleus | + |
| Ventral premammillary nucleus | + + |
| Supramammillary nucleus | + |
| Midbrain | |
| Nucleus of superior colliculus | + + |
| Brainstem | |
| Area postrema | + + + |
| Nucleus tractus solitarius | + + + |
| Periphery | |
| Adrenal medulla | + + |
| Uterus | NB |

The RTN plays an important role in the gating of sensory information into the cortex, in generating sleep spindles, a hallmark of slow wave sleep, and is implicated in the formation of absence seizure activity (reviewed in Danober et al., *Prog. Neurobiol.* 55:27–57 (1998) and McCormick et al., *Annu. Rev. Neurosci.* 20:185–215 (1997)). The RTN consists of predominantly GABAergic neurons, the activities of which are known to silence thalamocortical activity during spike-wave (absence) seizures, possibly contributing to the loss of consciousness during these states (see Steriade et al., *Cereb Cortex* 7:583–604 (1997) and Liu et al., *Brain Res.* 545:1–7 (1991)).

To determine whether GPR10 is expressed on the GABAergic neurons of the RTN, in situ double labeling using digoxigenin-GAD and $^{35}$-S-GPR10 probes was performed. For GAD (glutamic acid decarboxylase) double labeling, the samples were treated as described above, except hybridization included both $^{35}$S labeled GPR10 cRNA and digoxigenin labeled GAD cRNA (E. Jones, University of California, Irvine). Subsequent incubation with alkaline phosphatase conjugated anti-digoxigenin antibody, washes, and substrate development were preformed according to manufacturer's instructions (Genius kit, Roche). Emulsion dipped slides were not cresyl violet stained. Double labeling was detected by viewing GAD positivity with light microscopy and GPR10 labeling under dark field.

Figure 1C:
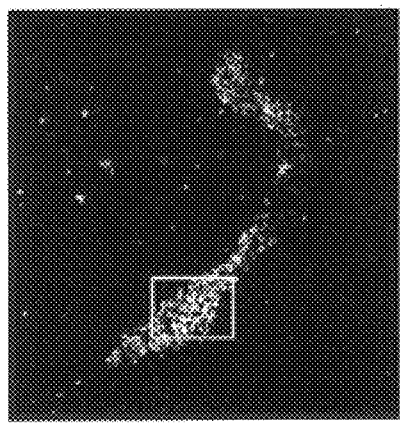
FIG. 1C shows expression of GPR10 RNA within the RTN.
Figure 1E:
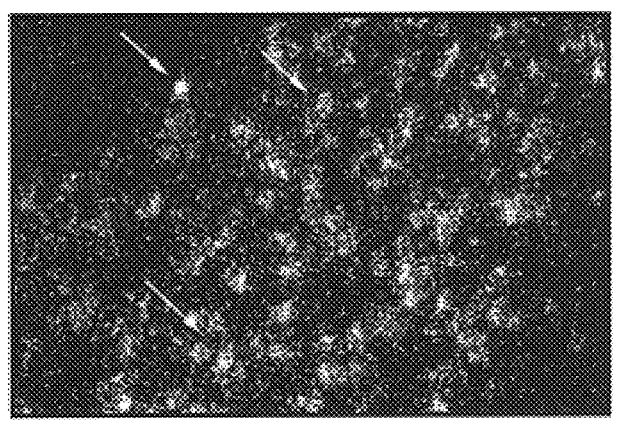
FIGS. 1E and 1F show higher magnification views of FIGS. 1C and 1D, respectively.
Figure 1D:
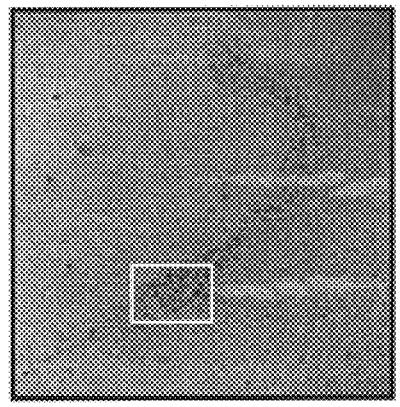
FIG. 1D shows labeling of GABAnergic neurons within the section of the RTN in FIG. 1C.
Figure 1F:
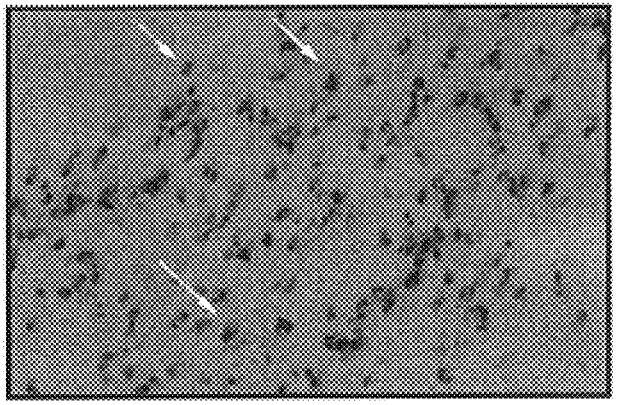

The distribution of GPR1O expresssion observed corresponded with the "shell" pattern seen for GAD labeling (see FIGS. 1C and 1D). Examining the labeled sections under higher magnification revealed that GPR10 expression overlaps with the GAD labeling of GABAergic neurons of the RTN (see FIGS. 1E and 1F).

Based on expression of GPR10 in the GABAnergic neurons of the RTN, it was predicted that PrRP modulates GABAergic output in the RTN.

EXAMPLE II

Interaction of GPR10 with AMPA Receptor-interacting Proteins

This example shows that GPR10 interacts with GRIP-like proteins through its cytoplasmic tail, and forms clusters with PICK1.

Figures 2A, 2B, 2C:
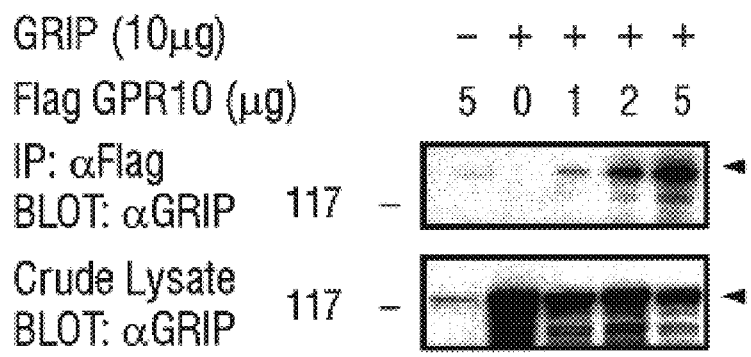
FIG. 2A shows an alignment of the amino acid sequence of the cytoplasmic tail of GPR:10 (SEQ ID NO:1) with the cytoplasmic tails of the AMPA receptor subunits GluR2 (SEQ ID NO:2) and GluR3 (SEQ ID NO:3).
FIG. 2B, top, shows an analysis of co-immunoprecipitation of GRIP with Flag-tagged GPR10 from transiently co-transfected HEK 293T cells.
FIG. 2C shows the C-terminal sequences of Flag GPR10 WT (SEQ ID NO:4) and its various mutations having the following sequence identifiers: del6 (SEQ ID NO:5); ΔLC (SEQ ID NO:6); T365A (SEQ ID NO:7); V366A (SEQ ID NO:8); S367A (SEQ ID NO:9); V368A (SEQ ID NO:10); V369A (SEQ ID NO:11); and I370A (SEQ ID NO:12).

An analysis of GPR10 sequence revealed that its carboxy-terminal tail contained a sequence motif of 4 amino acids (-SVVI) (SEQ ID NO:24) similar to those found in GluR2 and GluR3 subunits of AMPA receptors (FIG. 2A). The sequence -SVXI (X=any amino acid) has been shown to be critical for the binding of AMPA receptors to GRIP (Dong et al., *Nature* 386:279–284 (1997)), ABP (AMPA binding protein, also designated GRIP2) (Srivastava et al., *Neuron* 21:581–591 (1998); Dong et al., *J. Neurosci.* 19:6930–6941 (1999)), and PICK1 (Xia et al., *Neuron* 22:179–187 (1999)). GRIP, ABP and PICK1 are PDZ domain proteins which have been shown to be important for the proper targeting and scaffolding of AMPA receptors to the postsynaptic density (Craven et al., *Cell* 83:495–498 (1998); O'Brien et al., *Curr. Opin. Neurobiol.* 8:364–369 (1998)).

To determine whether GPR10 interacts with these proteins, incremental amounts of Flag-tagged GPR10 cDNA, or Flag-tagged GPR10 cDNA with C-terminal mutations, were transiently co-transfected by calcium phosphate transfection with fixed amounts of cDNA encoding GRIP, myc-tagged ABP, myc-tagged PSD95, or myc-tagged PICK1 in HEK 293T cells. Flag-tag and C-terminal mutations were introduced by PCR into GPR10 cDNA in pcDNA (Brian O'Dowd, U. Toronto), and sequences were confirmed by dideoxy cycle sequencing containing deaza-dGTP on an ALF-Express automated sequencer (Pharmacia). Myc-PICK1 was generated by PCR using PICK-1 Flag (Jeff Staudinger, GlaxoWellcome) as the template. GRIP cDNA in pRK/CMV was obtained from Richard Huganir (Johns Hopkins), and PSD-95 myc was obtained from Morgan Sheng (Harvard University).

Forty-eight hours after transfection, cells were washed once in PBS and lysed with IP buffer (1% triton X-100, 25 mM Tris, pH 7.4, 50 mM NaCl, 5 mM EDTA, 5 mM EGTA, 0.1 mM phenylmethylsulphonyl fluoride (PMSF), aprotinin, leupeptin, and bacitracin).

Immunoprecipitation was performed using 2 μg anti-Flag M2 antibody (Sigma) or 1 μg anti-myc antibody (Roche) followed by 25 μl protein G-agarose (Sigma).

Immunoprecipitation was carried out overnight at 4° C.

Immunoprecipitated proteins were resolved on SDS-PAGE, transferred to PVDF membrane. Western blotting was performed to detect GRIP using anti-GRIP antibody (1:1000). ABP-myc, PSD-95-myc, and PICK1-myc were detected using the monoclonal anti-myc antibody (1:500, Clontech).

Figure 2D:
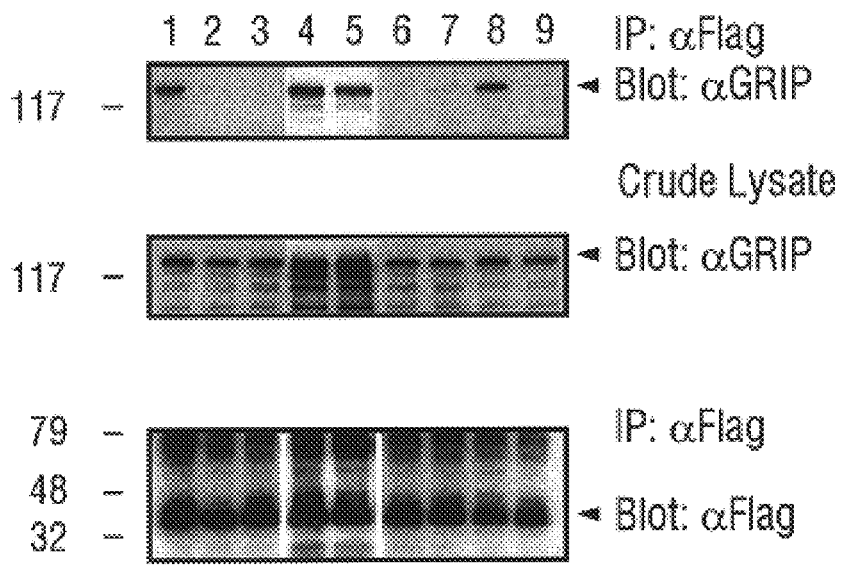
FIG. 2D, top, shows an analysis of co-immunoprecipitation of GRIP with Flag-tagged GPR10 mutants from transiently co-transfected HEK 293T cells.

As shown in FIG. 2B, increasing amounts of GRIP were co-immunoprecipitated with GPR10 as the amount of co-transfected GPR10 increased. The specificity of this interaction was demonstrated by introducing mutations at the COOH-terminal tail of Flag-tagged GPR10 (FIG. 2C). Deletion of the last six amino acids, as well as substituting the last 4 amino acids with unrelated sequences completely abolished GRIP co-immunoprecipitation (FIG. 2D). Furthermore, alanine point mutations were introduced in place of each of the last six amino acids and revealed that threonine-365, valine-366, and valine-369 were not important for GRIP interaction, while serine-367, valine-368, and isoleucine-370 were critical (FIG. 2D), consistent with results of similar studies performed with AMPA receptors (Dong et al., *Nature* 386:279–284 (1997); Srivastava et al., *Neuron* 21:581–591 (1998))

These results indicate that the C-terminal tail of GPR10 contains a sequence that can interact with GRIP or GRIP-like proteins.

Figure 2E:
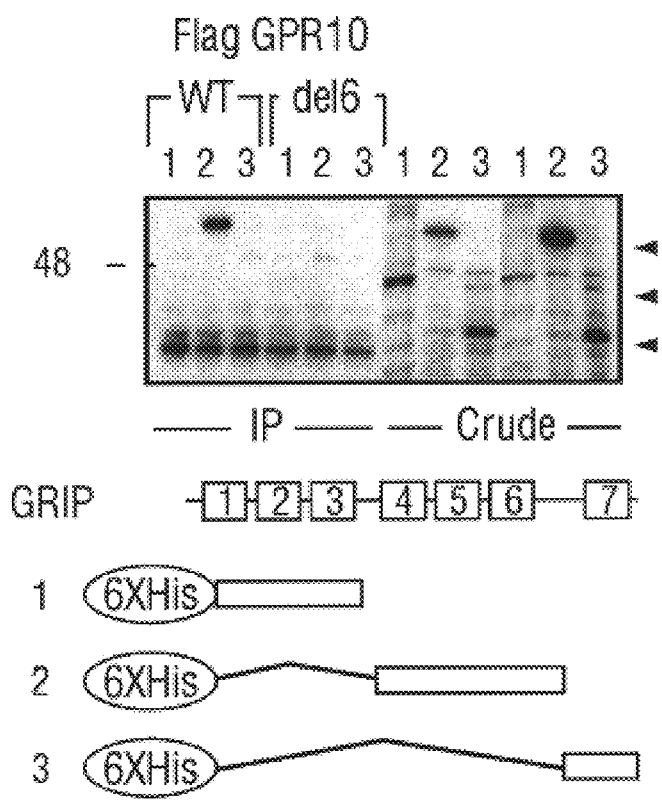
FIG. 2E shows an analysis of co-immunoprecipitation of various 6X-His tagged GRIP PDZ domain polypeptides with wild-type or C-terminally deleted (del6) forms of Flag-tagged GPR10.

GRIP is a large cytoplasmic protein containing seven PDZ domains. A previous study has shown that GluR2 and GluR3 interact with the central three PDZ domains of GRIP (domains 4–6) (Dong et al., *Nature* 386:279–284 (1997)). To determine whether GPR10 interacts with the same domains, 6X-Histidine tagged GRIP PDZ domain segments 1–3, 4–6 or 7, generated by PCR, were co-transfected and immuno-precipitated with Flag-tagged GPR10. As shown in FIG. 2E, GPR10 interacted with PDZ domains 4–6 of GRIP. This interaction is specific, since the C-terminally deleted GPR10 mutant (del6) was unable to interact.

Figure 2F:
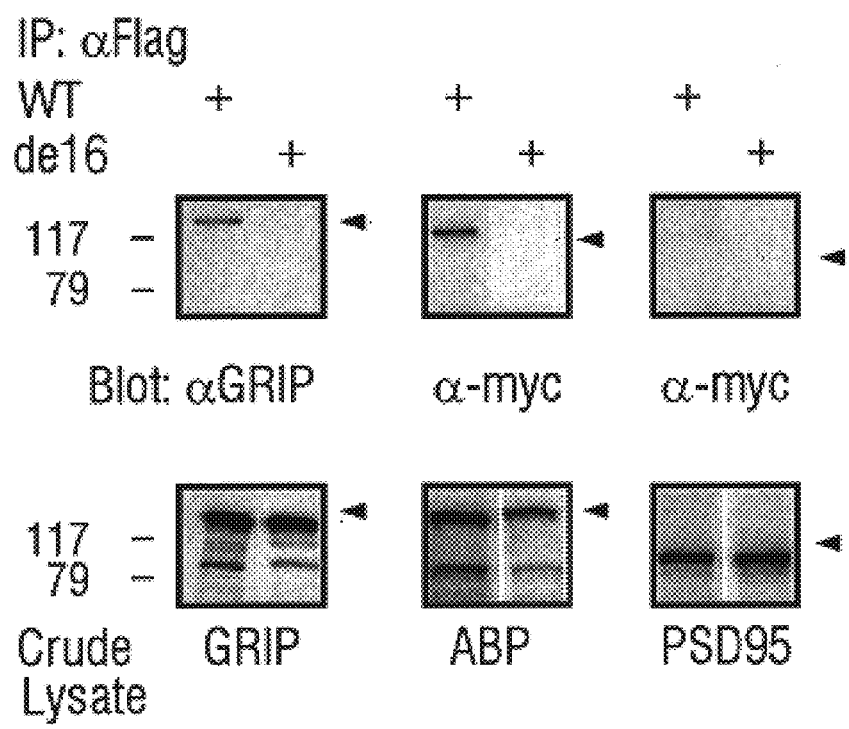
FIG. 2F, top, shows an analysis of co-immunoprecipition of transiently transfected GRIP, myc-tagged ABP or myc-tagged PSD95 with Flag-tagged GPR10 from HEK 293T cells stably expressing wild-type or del6 forms of Flag-tagged GPR10.

Besides GRIP, other PDZ domain-containing proteins have been demonstrated to interact with the same C-terminal residues of AMPA receptors. To determine whether GPR10 interacts specifically with AMPA receptor interacting proteins, myc-tagged ABP and myc-tagged PSD95 were transfected into cell lines expressing wild type and mutant Flag-tagged GPR10. As shown in FIG. 2F, GPR10 interacted with the AMPA receptor binding protein ABP, but not with PSD95, a PDZ domain protein important for NMDA receptor trafficking to and anchoring at glutaminergic synapses (Gomperts, *Cell* 84:659–662 (1996)).

Figure 3A:
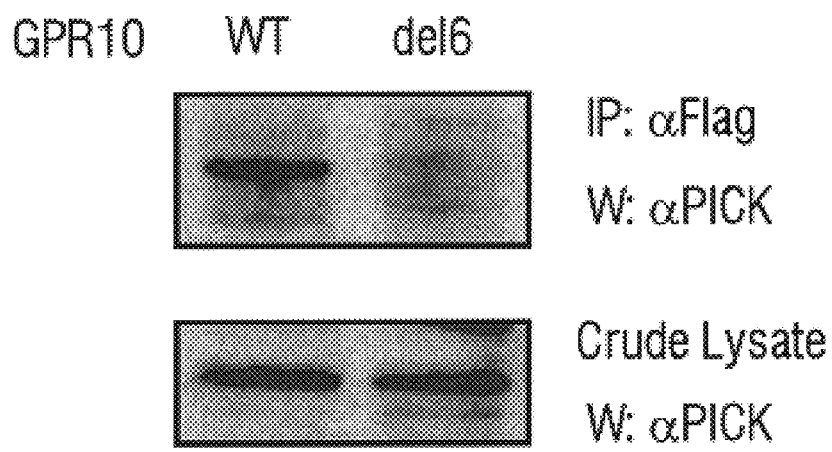
FIG. 3A shows an analysis of co-immunoprecipitation of myc-tagged PICK1 and Flag-tagged GPR10 from cotransfected HEK 293T cells.

PICK1, originally identified as a PKCα interacting protein (Staudinger et al., *J. Biol. Chem.* 272:32019–32024 (1997)), is another PDZ domain protein recently shown to interact with the GluR2 subunit of AMPA receptors. Unlike GRIP and ABP, PICK1 is the only AMPA receptor interacting protein that forms intracellular and surface aggregates with GluR2 subunits (but not GluR1) in heterologous cell lines (Xia et al., *Neuron* 22:179–187 (1999); Dev et al., *Neuropharmacology* 38:635–644 (1999)). To determine whether GPR10 could mimic these characteristics, co-immunoprecipitation was performed on cells co-transfected with myc-tagged PICK1 and Flag-tagged GPR10. As shown in FIG. 3A, immunoprecipitation of GPR10 caused a concomitant precipitation of PICK1 protein, an effect which was not observed using the mutant (del6) receptor.

Immunocytochemistry was also performed as follows. COS7 cells were transfected with LipofectAMINE (Gibco-BRL) using 6 µg DNA. Twenty-four hours after transfection, cells were trypsinized and seeded onto poly-D-lysine coated glass coverslips. All immunocytochemical analysis was done 48 hours after transfection. Anti-PICK1 antibody (1:500) was incubated overnight at 4° C., whereas anti-myc monoclonal antibody (1:500, Clontech) was incubated for 2 hours at room temperature. All chromophore conjugated secondary antibodies were incubated for 1 hour at room temperature.

Coverslips were mounted on Vectashield mounting media (Vector laboratories), and visualized at 60X on a Nikon fluorescence microscope.

COS7 cells transfected with either GPR10 and PICK1 alone exhibited diffuse cytoplasmic staining, as shown in FIG. 3B and 3C. However, cells co-expressing both proteins exhibited intracellular (FIG. 3D) as well as surface clustering (FIG. 3E) of GPR10 and PICK1. Such clustering is contingent upon direct protein-protein interaction between the COOH-terminal residues of GPR10 and the PDZ domain of PICK1, since deleting the last six residues of GPR10 as well as mutating critical residues within the PDZ domain of PICK1 (K27D28AA) (Staudinger et al., *J. Biol. Chem.* 272:32019–32024 (1997)) obliterates clustering (FIGS. 3F and 3G).

These results strongly support the possibility that GRIP-like molecules, besides interacting with AMPA receptors at the postsynaptic density, could help, recruit molecules such as GPR10 and PKC to form a signal transduction complex with AMPA receptors. The assembly of such proteins in microdomains forms an efficient network by which activation of one protein could modulate other proteins in the complex.

Examples of G protein coupled receptors (GPCRs) affecting channel function through direct or indirect interactions with PDZ domain proteins have been reported. For instance, the β2 adrenergic receptor (β2AR) indirectly activates the $Na^+/H^+$ exchanger (NHE3) by binding to the PDZ domain protein NHERF, which normally inhibits NHE3 activity (Hall et al., *Nature* 392:626–630 (1998)). This interaction is mediated through the COOH-terminal sequence of β2AR in an agonist dependent manner. *Drosophila rhodopsin* indirectly affects $Ca^{++}$ influx through a TRP calcium channel via a Gq/PLC/eye PKC phototransduction cascade organized by the PDZ domain protein inaD (Tsunoda et al., *Nature* 388:243–249 (1997)). Finally, the CRF-R1 receptor has also been shown to interact with PSD95 through an analogous COOH terminal motif found also in NR2 subunits of NMDA receptors (Gaudriault et al., *Society for Neuroscience Abstract* 24:570 (1998)).

EXAMPLE III

Effect of PrRP on Thalamic Oscillatory Activity

This example shows that PrRP reduces AMPA receptor-mediated, but not NMDA receptor-mediated, thalamic oscillatory activity.

Given that GPR10 interacts with AMPA receptor associated molecules it was postulated that GPR10 receptor activation may affect AMPA receptor signaling. Such an effect would most likely influence oscillatory activity produced in the RTN since glutamatergic inputs are critical for maintaining this network function (Salt et al., *Prog. Neurobiol.* 48:55–72 (1996)). To test this hypothesis, extracellular recordings were made from the RTN in thalamic slices.

Horizontal thalamic slices (400 µm) were prepared from Sprague-Dawley rats (postnatal rats 13–15) using a vibratome (Leica, VT1OOOS). The slices were transferred to a recording chamber after at least 1 hr recovery, and were superfused with artificial cerebrospinal fluid (aCSF) equilibrated with 95% $O_2$/5% $CO_2$ at 0.5 ml/mm. The aCSF contained (in mM): NaCl 126, KCl 2.5, $NaH_2PO_4$ 1.25, $CaCl_2$ 2, $MgSO_4$ 0.63, $NaHCO_3$ 26, and glucose 10. All experiments were carried out in the presence of 10 µM bicuculline maleate and cytochrome c (100 µg/ml) at 34° C. A glass electrode filled with 2 M NaCl was positioned in the nucleus of reticular thalamus (RTN), and extracellular recording was made in response to stimulation of the internal capsule (1–50 µA) every 20–30 sec. After establishing stable oscillatory activity, PrRP was applied for 15–20 min. Paired Student's t-Test was used for statistical analysis. The data were digitized at 1–5 kHz with the Neuronal Activity Acquisition Program (Eclectek Enterprise).

Figure 4A:
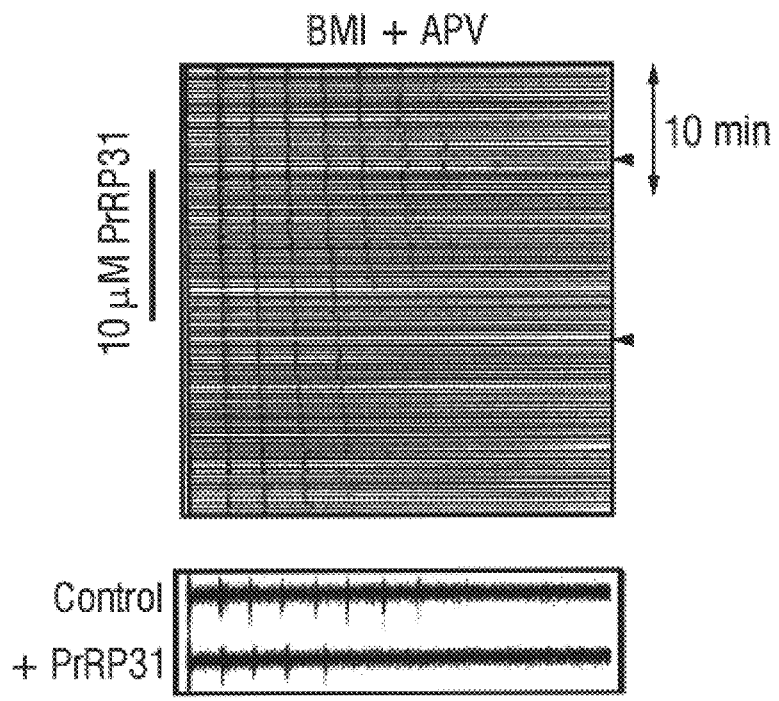
FIG. 4A shows the effect of PrRP on AMPA receptor-mediated thalamic oscillatory activity.

In the representative experiments shown in FIG. 4, each block shows 90–100 sweeps of 5 set duration, separated by 20–30 set, and each sweep represents the oscillatory activity in response to a single stimulation pulse delivered to the internal capsule. The bar on the left indicates the duration of peptide application. The traces at the bottom show representative responses before and in the presence of PrRP, taken at the time points indicated with arrow heads.

Under $GABA_A$ receptor blockade and reduced $Mg^{2+}$, stimulation of the internal capsule induced 4–12 spindle-like discharges oscillating at 3–4 Hz (FIG. 4), as previously reported (Ulrich et al., *Neuron* 15,909–918 (1995)). In order to isolate the AMPA receptor driven-oscillation, slices were equilibrated with the NMDA receptor antagonist D,L-aminophosphonovaleric acid (DL-APV).

Figure 4B:
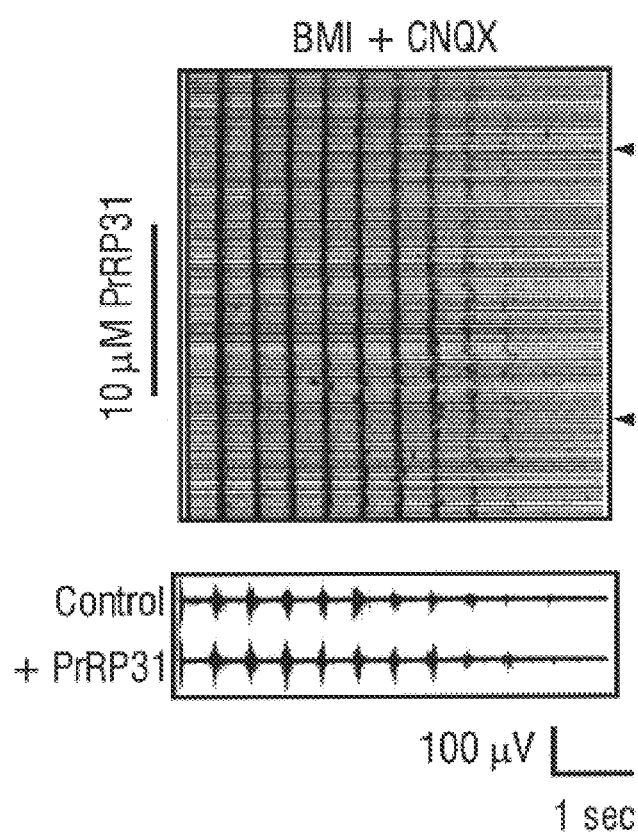
FIG. 4B shows the effect of PrRP on NMDA receptor-mediated thalamic oscillatory activity.
Figure 4C:
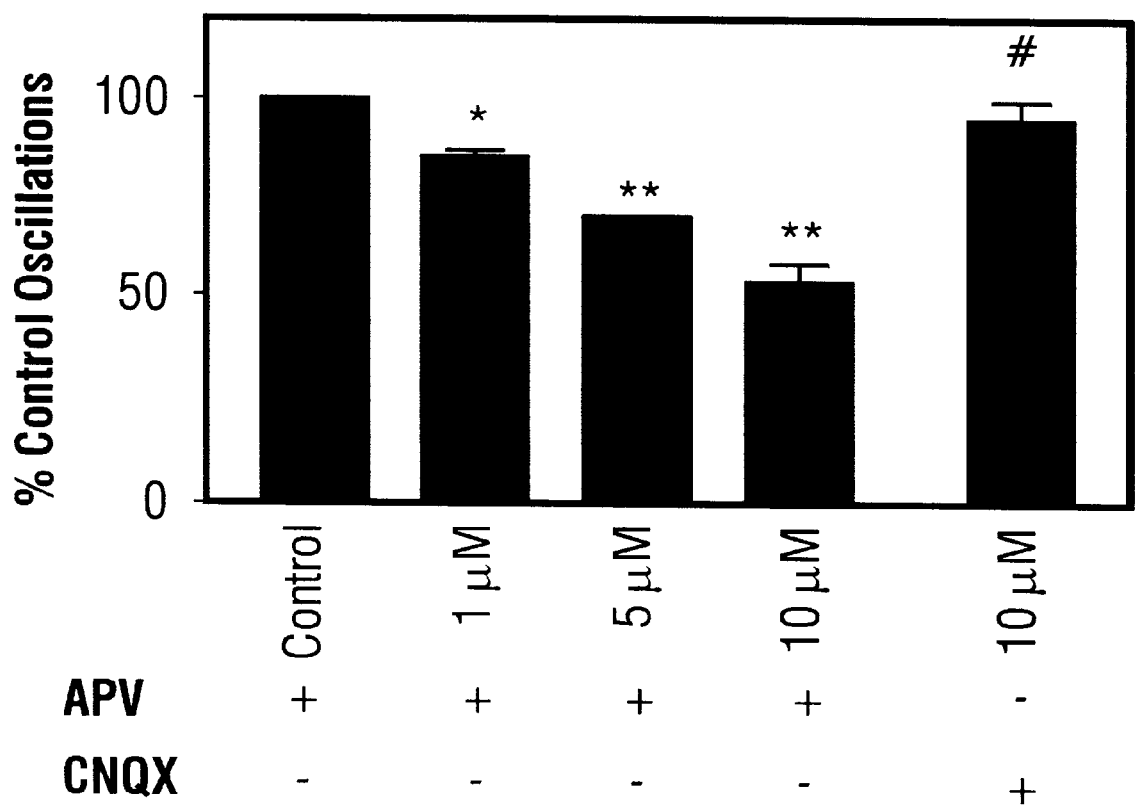
FIG. 4C shows the concentration dependent effect of PrRP on thalamic oscillatory activity. *, $p<0.01$; **, $p<0.001$, paired Student's t-Test.

Application of PrRP significantly reduced the umber of oscillations (FIG. 4A) and the effect was concentration dependent (FIG. 4C). Maximum suppression, approximately 40%, was obtained at 10 µM since higher concentrations (20 µM) produced a comparable degree of inhibition. In the experiments depicted in FIG. 4C, the number of oscillations in the presence of PrRP was normalized to that of the pre-peptide response. Columns represent the mean +/-S.E. of 12 (pre-peptide), 6 (10 µM), 2 (5 µM), and 4 (1 µM) experiments, respectively.

It was next investigated whether the suppression of RTN oscillatory activity by PrRP is the consequence of AMPA receptor modulation or some general cellular effect. If the latter, thalamic oscillations driven by NMDA receptors should be similarly reduced by PrRP. The above experiment was thus repeated in a low $Mg^{2+}$ (0.1 mM)-aCSF containing 10 µM of the AMPA receptor antagonist CNQX. As shown in FIGS. 4B and 4C (right column, n=4), 10 µM PrRP had no discernible effect on oscillation under these circumstances.

In summary, the results described in this example indicate that PrRP reduces thalamic oscillatory activity by selectively modulating AMPA receptors.

EXAMPLE IV

Effect of PrRP on Absence Seizures

This example shows that PrRP suppresses seizure activity in GAERS.

Spindle wave oscillations generated in the brain slice correlate well with the activity seen during slow wave sleep as well as during an episode of absence seizure attack (Danober et al., Prog. Neurobiol. 55:27–57 (1998); McCormick et al., Annu. Rev. Neurosci. 20:185–215 (1997)). To assay whether the in vitro effects of PrRP on thalamic oscillations reflect in vivo efficacy, an animal model of absence seizure that present with spontaneous spike-and-wave discharges (SWD) was used.

The GAERS (Genetic Absence Epilepsy Rats from Strasbourg) is a rat strain that exhibits recurrent seizure activity characterized by bilateral and synchronous SWD and behavioral arrest (Danober et al., Prog. Neurobiol. 55:27–57 (1998)). Drugs used to treat absence seizure in humans have been shown to be effective in suppressing seizure-activity in this model (Danober et al., Prog. Neurobiol. 55:27–57 (1998); Gower et al., Epilepsy Res. 22:207–213 (1995)).

Electroencephalogram (EEG) recordings and intracerebroventricular (ICV) injection into GAERS were performed essentially as described in Liu et al., Brain Res. 545:1–7 (1991). Briefly, six male GAERS (300–400 g) were implanted stereotaxically (AP=−0.8, ML=1.2, CV=3 mm, with bregma as reference) with a permanent stainless steel cannula under pentobarbital anesthesia (40 mg/kg i.p.). All rats were also implanted bilaterally with 4 stainless-steel electrodes at the frontal and parietal cortex and connected to a microconnector. Both the guide cannulae and EEG electrodes were anchored to the skull using retaining screws and dental acrylic cement.

After one week of recovery, stainless steel injection cannulae were introduced into the guide cannulae so as to extend 2–4 mm beyond their tips. Injection cannulae were connected to a 10 $\mu$l microsyringe driven by a pump. Five microliters saline or peptides at various concentrations were microinjected over 1 min through the cannulae while taking EEG recordings continuously throughout the duration of the experiment, in freely moving animals. During EEG recordings the rats were carefully watched and were prevented from falling asleep by gentle sensory stimulation. Seizure frequency was determined as a cumulative duration of spike and wave discharges per consecutive 20 minute periods (seconds of seizure activity per 20 minute recording) after the initial injection. Statistical analysis was performed using the Wilcoxon test.

Figure 5A:
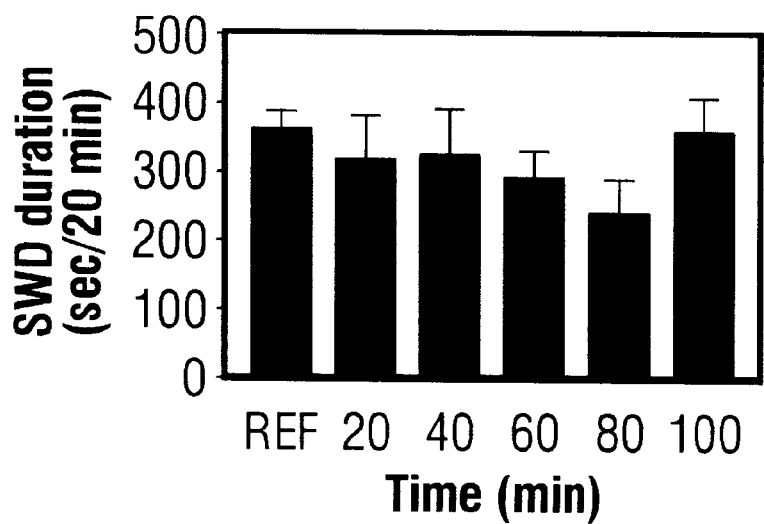
FIG. 5 shows seizure frequency in GAERS rats (n=6), expressed as cumulative duration of spike and wave discharges (SWD) at 20 min intervals after injection of aCSF control (FIG. 5A) or injection of various PrRP concentrations (FIGS. 5B–D). "REF"=reference duration of spontaneous seizure activity before injection.
Figure 5B:
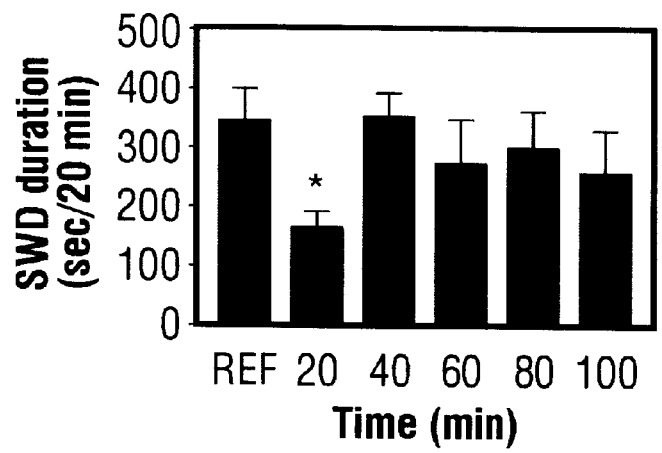
Figure 5C:
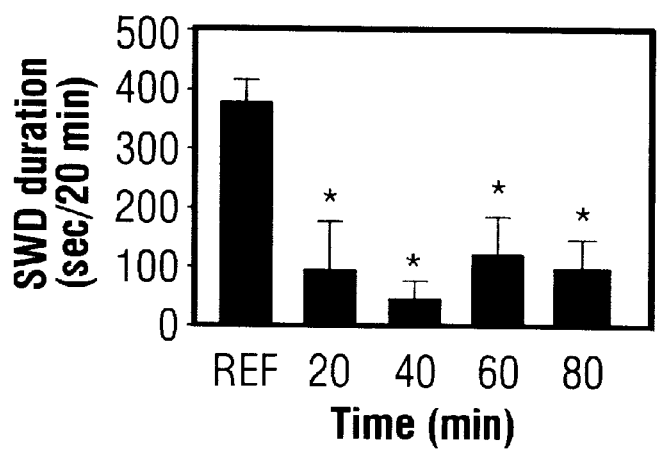
Figure 5D:
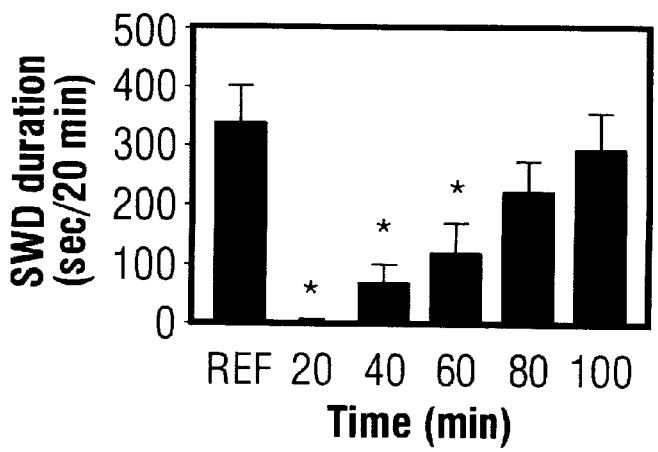

PrRP was administered intracerebroventricularly into GAERS rats. EEG was taken throughout the course of the experiment and time spent in seizures (spike and wave discharges (SWD) duration) was tabulated for 20 minute intervals from the initial infusion of either aCSF control or various peptide concentrations. Data from six animals receiving the same treatment were pooled. In comparison to aCSF control, PrRP was able to dose-dependently suppress seizure activity in this animal model (FIGS. 5A–5D). At 10 nmol PrRP, the SWD duration was reduced by half for the first 20 minutes, and returned to baseline after 40 minutes (FIG. 5B). At higher peptide concentrations, seizure activity was reduced more significantly (i.e. by 75% at 50 nmol (FIG. 5C), and by almost 100% at 100 nmol at 20 minutes (FIG. 5D)). This seizure suppressing activity remained significant 60 to 80 minutes after peptide injection. No other mobility or behavioral changes were observed at all peptide concentrations.

The results described above demonstrate that PrRP is effective in suppressing absence seizures.

In summary, the results described in Examples I–IV demonstrate that GPR10, the PrRP receptor, is highly expressed in the GABAergic neurons of the RTN; that GPR10 contains structural motifs that allow it to interact with PDZ domain-containing proteins; that application of PrRP specifically reduces AMPA receptor mediated oscillatory activity; and that PrRP suppresses absence seizures. These results show a novel role of GPR10 and PrRP in regulating thalamic networks and implicate GPR10 as a-potential therapeutic target in the treatment of disorders associated with the RTN, including absence seizures and sleep disorders.

EXAMPLE V

Whole Cell Electrophysiological Recordings from RTN Neurons

This example shows an exemplary method of determining the ability of a compound to modulate AMPA receptor signaling.

Horizontal slices (200 $\mu$m) are prepared from postnatal Sprague Dawley rats (P13–P15). After at least 1 hr of incubation at room temperature in artificial cerebrospinal fluid (aCSF) containing (in mM): NaCl 126, KCl 2.5, $NaH_2PO_4$ 1.25, $CaCl_2$ 2, $MgSO_4$ 2, $NaHCO_3$ 26, and glucose 10), slices are transferred to a recording chamber and submerged in low $Mg^{2+}$-aCSF (0.63 mM) equilibrated with 95% $O_2$/5% $CO_2$. Whole cell recording are made from neurons in the nucleus of reticular thalamus at room temperature in low $Mg^{2+}$-aCSF containing 100 mM DL 2-aminophosphonovaleric acid (APV), 10 mM bicuculline maleate (BMI), and 100 mg/ml cytochrome c. The flow rate is 2 ml/min. Patch electrodes are pulled from borosilicate glass (2–3 MOhm) and filled with a pipette solution containing (in mM): CsCl 135, MgCl 2, EGTA 10, HEPES 10, ATP 10, and QX314 5 (pH 7.3). Excitatory postsynaptic currents (EPSCS) are recorded in response to activation of the internal capsule. The holding current and access resistance are constantly monitored and the holding potential is maintained at −70 mV throughout the experiment. After establishing a stable baseline, a compound is applied to the perfusion line for 15 minutes. The data is digitized and analyzed offline. Aspects of the method are described in further detail in Cox et al., J. Neurophysiol. 74:990–1000 (1995).

EXAMPLE VI

Whole Cell Ion Influx Assays

This example shows a further exemplary method of determining the ability of a compound to modulate AMPA receptor signaling.

The method uses cells that express both AMPA receptors and PrRP receptors, such as cell lines (e.g.

HEK 293 cells) transiently or stably transfected with AMPA receptors and GPR10, or RTN neurons. A determination is made as to effect of the test compound on calcium ion or sodium ion influx in response to AMPA receptor agonists. The method is amenable to either low-throughput (e.g. light microscopy) or high-throughput (e.g. FLIPR) assays.

AMPA receptor agonists include, for example, AMPA (e.g. s-AMPA zwitterion, at a concentration of about 10 $\mu$M) or glutamate (at a concentration of about 10 mM). Optionally, an assay can be performed in the presence of an AMPA receptor antagonist (e.g. CNQX at a concentration of about 20 $\mu$M), for example to ensure that any response is dependent on AMPA receptors. Since AMPA receptors desensitize rapidly upon activation, a drug such as cyclothiazide can be added, at a concentration of about 100 μM. The addition of cyclothiazide is expected to reduce the desensitization rate and potentiate AMPA signals by a factor of about 200 fold. The use of such antagonists and modulators to isolate or stabilize AMPA signals are well known in the art.

To determine whether PrRP or a PrRP functional analog modulates AMPA receptor signaling, the test compound is added to the cells, followed by an AMPA receptor agonist. The relative amplitude change of calcium or sodium influx through the AMPA receptors is a measure of the ability of the compound to modulate AMPA receptor signaling.

In calcium ion influx assays, PrRP can be added to the cells for a sufficient period (e.g. about 3 to 5 minutes) to desensitize GPR10-mediated calcium signals and more clearly determine specific AMPA receptor mediated signals. Calcium channels can be blocked, if desirable, with calcium channel blockers known in the art. Calcium ion influx in response to AMPA receptor activation can be determined using fluorescent sensitive calcium indicators (e.g. Fluo-3 and the like), by visualizing single cells under light microscopy. Alternatively, particularly where high-throughput screening is desired, calcium influx in response to AMPA receptor activation can be determined using a fluorometric imaging plate reader (FLIPR), which allows rapid detection of changes in intracellular calcium levels.

Likewise, sodium ion influx in response to AMPA receptor activation can be determined using fluorescent sensitive sodium indicators (e.g. SBFI and the like, available from Molecular Probes), either by visualizing single cells under light microscopy or by adapting FLIPR technology.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

What is claimed is:

1. A method of identifying a compound for controlling absence seizures in a mammal, comprising:
   (a) providing a compound that is a Prolactin-Releasing Peptide (PrRP) or PrRP functional analog;
   (b) administering said compound to a mammal susceptible to absence seizures; and
   (c) determining the ability of said compound to control absence seizures in a mammal, wherein a compound that controls absence seizures is identified.

2. The method of claim 1, wherein step (a) comprises contacting a PrRP receptor with one or more candidate compounds under conditions wherein PrRP promotes a predetermined signal, identifying a compound that promotes production of said predetermined signal, and providing said compound.

3. The method of claim 2, wherein said predetermined signal is selected from the group consisting of calcium ion mobilization and arachadonic acid metabolite release.

4. The method of claim 2, wherein said PrRP receptor is GPR10.

5. The method of claim 2, wherein said one or more candidate compounds comprises greater than about 100 compounds.

6. The method of claim 1, wherein step (a) comprises contacting a PrRP receptor with one or more candidate compounds under conditions wherein PrRP binds said PrRP receptor, identifying a compound that binds said PrRP receptor, and providing said compound.

7. The method of claim 6, wherein said PrRP receptor is GPR10.

8. The method of claim 6, wherein said one or more candidate compounds comprises greater than about 100 compounds.

9. The method of claim 1, wherein step (a) comprises contacting a PrRP receptor with one or more candidate compounds under conditions wherein PrRP promotes interaction of PrRP receptor with an Alpha-amino-3-hydroxy-5-methyl-4-isoxazolepropionic acid (AMPA) receptor associated protein, identifying a compound that promotes said interaction, and providing said compound.

10. The method of claim 9, wherein said AMPA receptor associated protein is selected from the group consisting of GRIP, GRIP2 and PICK1.

11. The method of claim 1, wherin said compound is administered to a mammal selected from the group consisting of a human, a non-human primate, a rat and a mouse.

12. The method of claim 11, wherein said mammal is a Genetic Absence Epilepsy Rat from Strasbourg (GAERS).

13. The method of claim 1, wherein said compound that controls absence seizures is a compound that reduces the frequency, number, duration or intensity of absence seizures.

* * * * *

UNITED STATES PATENT AND TRADEMARK OFFICE
CERTIFICATE OF CORRECTION

PATENT NO. : 6,383,764 B1
DATED : May 7, 2002
INVENTOR(S) : Civelli et al.

It is certified that error appears in the above-identified patent and that said Letters Patent is hereby corrected as shown below:

Column 34,
Line 57, please delete "wherin" and replace therefore with -- wherein --.

Signed and Sealed this

Twenty-fifth Day of May, 2004

JON W. DUDAS
*Acting Director of the United States Patent and Trademark Office*

SEQUENCE LISTING

```
<160> NUMBER OF SEQ ID NOS: 24

<210> SEQ ID NO 1
<211> LENGTH: 29
<212> TYPE: PRT
<213> ORGANISM: Homo Sapien

<400> SEQUENCE: 1

Phe Arg Glu Glu Leu Arg Lys Leu Leu Val A la Trp Pro Arg Lys Ile
1               5                   10                  15

Ala Pro His Gly Gln Asn Met Thr Val Ser V al Val Ile
            20                  25

<210> SEQ ID NO 2
<211> LENGTH: 29
<212> TYPE: PRT
<213> ORGANISM: Homo Sapien

<400> SEQUENCE: 2

Asn Pro Ser Ser Ser Gln Asn Ser Gln Asn P he Ala Ala Thr Tyr Lys
1               5                   10                  15

Glu Gly Tyr Asn Tyr Tyr Gly Ile Glu Ser V al Lys Ile
            20                  25

<210> SEQ ID NO 3
<211> LENGTH: 29
<212> TYPE: PRT
<213> ORGANISM: Homo Sapien

<400> SEQUENCE: 3

Phe Lys Pro Ala Pro Ala Thr Asn Thr Gln A sn Tyr Ala Thr Tyr Arg
1               5                   10                  15

Glu Gly Tyr Asn Val Tyr Gly Thr Glu Ser V al Lys Ile
            20                  25

<210> SEQ ID NO 4
<211> LENGTH: 12
<212> TYPE: PRT
<213> ORGANISM: Homo Sapien
```

<400> SEQUENCE: 4

Pro His Gly Gln Asn Met Thr Val Ser Val Val Ile
1               5                   10

<210> SEQ ID NO 5
<211> LENGTH: 6
<212> TYPE: PRT
<213> ORGANISM: Artificial Sequence
<220> FEATURE:
<223> OTHER INFORMATION: human GPR10 variant

<400> SEQUENCE: 5

Pro His Gly Gln Asn Met
1               5

<210> SEQ ID NO 6
<211> LENGTH: 12
<212> TYPE: PRT
<213> ORGANISM: Artificial Sequence
<220> FEATURE:
<223> OTHER INFORMATION: human GPR10 variant

<400> SEQUENCE: 6

Pro His Gly Gln Asn Met Thr Val Pro Arg Pro Ala
1               5                   10

<210> SEQ ID NO 7
<211> LENGTH: 12
<212> TYPE: PRT
<213> ORGANISM: Artificial Sequence
<220> FEATURE:
<223> OTHER INFORMATION: human GPR10 variant

<400> SEQUENCE: 7

Pro His Gly Gln Asn Met Ala Val Ser Val Val Ile
1               5                   10

<210> SEQ ID NO 8
<211> LENGTH: 12
<212> TYPE: PRT
<213> ORGANISM: Artificial Sequence
<220> FEATURE:
<223> OTHER INFORMATION: human GPR10 variant

<400> SEQUENCE: 8

Pro His Gly Gln Asn Met Thr Ala Ser Val Val Ile
1               5                   10

<210> SEQ ID NO 9
<211> LENGTH: 12
<212> TYPE: PRT
<213> ORGANISM: Artificial Sequence
<220> FEATURE:
<223> OTHER INFORMATION: human GPR10 variant

<400> SEQUENCE: 9

Pro His Gly Gln Asn Met Thr Val Ala Val Val Ile
1               5                   10

<210> SEQ ID NO 10
<211> LENGTH: 12
<212> TYPE: PRT
<213> ORGANISM: Artificial Sequence
<220> FEATURE:
<223> OTHER INFORMATION: human GPR10 variant

```
<400> SEQUENCE: 10

Pro His Gly Gln Asn Met Thr Val Ser Ala Val Ile
1               5                   10

<210> SEQ ID NO 11
<211> LENGTH: 12
<212> TYPE: PRT
<213> ORGANISM: Artificial Sequence
<220> FEATURE:
<223> OTHER INFORMATION: human GPR10 variant

<400> SEQUENCE: 11

Pro His Gly Gln Asn Met Thr Val Ser Val Ala Ile
1               5                   10

<210> SEQ ID NO 12
<211> LENGTH: 12
<212> TYPE: PRT
<213> ORGANISM: Artificial Sequence
<220> FEATURE:
<223> OTHER INFORMATION: human GPR10 variant

<400> SEQUENCE: 12

Pro His Gly Gln Asn Met Thr Val Ser Val Val Ala
1               5                   10

<210> SEQ ID NO 13
<211> LENGTH: 31
<212> TYPE: PRT
<213> ORGANISM: Bos taurus

<400> SEQUENCE: 13

Ser Arg Ala His Gln His Ser Met Glu Ile Arg Thr Pro Asp Ile Asn
1               5                   10                  15

Pro Ala Trp Tyr Ala Gly Arg Gly Ile Arg Pro Val Gly Arg Phe
            20                  25                  30

<210> SEQ ID NO 14
<211> LENGTH: 31
<212> TYPE: PRT
<213> ORGANISM: Rattus

<400> SEQUENCE: 14

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 15
<211> LENGTH: 31
<212> TYPE: PRT
<213> ORGANISM: Homo Sapien

<400> SEQUENCE: 15

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 16
<211> LENGTH: 20
<212> TYPE: PRT
<213> ORGANISM: Bos taurus
```

```
<400> SEQUENCE: 16

Thr Pro Asp Ile Asn Pro Ala Trp Tyr Ala Gly Arg Gly Ile Arg Pro
1               5                   10                  15

Val Gly Arg Phe
            20

<210> SEQ ID NO 17
<211> LENGTH: 20
<212> TYPE: PRT
<213> ORGANISM: Rattus

<400> SEQUENCE: 17

Thr Pro Asp Ile Asn Pro Ala Trp Tyr Thr Gly Arg Gly Ile Arg Pro
1               5                   10                  15

Val Gly Arg Phe
            20

<210> SEQ ID NO 18
<211> LENGTH: 20
<212> TYPE: PRT
<213> ORGANISM: Homo Sapien

<400> SEQUENCE: 18

Thr Pro Asp Ile Asn Pro Ala Trp Tyr Ala Ser Arg Gly Ile Arg Pro
1               5                   10                  15

Val Gly Arg Phe
            20

<210> SEQ ID NO 19
<211> LENGTH: 7
<212> TYPE: PRT
<213> ORGANISM: Artificial Sequence
<220> FEATURE:
<223> OTHER INFORMATION: human  PrRP variant
<221> NAME/KEY: VARIANT
<222> LOCATION: (1)...(7)
<223> OTHER INFORMATION: Xaa = Any Amino Acid

<400> SEQUENCE: 19

Xaa Arg Pro Val Gly Arg Phe
1               5

<210> SEQ ID NO 20
<211> LENGTH: 7
<212> TYPE: PRT
<213> ORGANISM: Artificial Sequence
<220> FEATURE:
<223> OTHER INFORMATION: human  PrRP variant
<221> NAME/KEY: VARIANT
<222> LOCATION: (1)...(7)
<223> OTHER INFORMATION: Xaa = Any Amino Acid

<400> SEQUENCE: 20

Ile Arg Xaa Val Gly Arg Phe
1               5

<210> SEQ ID NO 21
<211> LENGTH: 7
<212> TYPE: PRT
<213> ORGANISM: Artificial Sequence
<220> FEATURE:
<223> OTHER INFORMATION: human PrRP variant
<221> NAME/KEY: VARIANT
<222> LOCATION: (1)...(7)
<223> OTHER INFORMATION: Xaa = Any Amino Acid
```

```
-continued

<400> SEQUENCE: 21

Ile Arg Pro Xaa Gly Arg Phe
1               5

<210> SEQ ID NO 22
<211> LENGTH: 7
<212> TYPE: PRT
<213> ORGANISM: Artificial Sequence
<220> FEATURE:
<223> OTHER INFORMATION: human PrRP variant
<221> NAME/KEY: VARIANT
<222> LOCATION: (1)...(7)
<223> OTHER INFORMATION: Xaa = Any Amino Acid

<400> SEQUENCE: 22

Ile Arg Pro Val Gly Arg Xaa
1               5

<210> SEQ ID NO 23
<211> LENGTH: 7
<212> TYPE: PRT
<213> ORGANISM: Homo Sapien

<400> SEQUENCE: 23

Ile Arg Pro Val Gly Arg Phe
1               5

<210> SEQ ID NO 24
<211> LENGTH: 4
<212> TYPE: PRT
<213> ORGANISM: Homo Sapien

<400> SEQUENCE: 24

Ser Val Val Ile
1
```